(12) United States Patent
Parkos

(10) Patent No.: US 7,282,556 B2
(45) Date of Patent: Oct. 16, 2007

(54) POLYNUCLEOTIDES AND POLYPEPTIDES RELATING TO THE MODULATION OF SIRPα-CD47

(75) Inventor: Charles A. Parkos, Norcross, CA (US)

(73) Assignee: Emory University, Atlanta, GA (US)

( * ) Notice: Subject to any disclaimer, the term of this patent is extended or adjusted under 35 U.S.C. 154(b) by 287 days.

(21) Appl. No.: 10/473,495

(22) PCT Filed: May 15, 2002

(86) PCT No.: PCT/US02/18531

§ 371 (c)(1),
(2), (4) Date: Sep. 26, 2003

(87) PCT Pub. No.: WO02/092784

PCT Pub. Date: Nov. 21, 2002

(65) Prior Publication Data

US 2004/0147731 A1  Jul. 29, 2004

Related U.S. Application Data

(60) Provisional application No. 60/291,050, filed on May 15, 2001.

(51) Int. Cl.
*A61K 38/04* (2006.01)
(52) U.S. Cl. .................................. 530/327
(58) Field of Classification Search ................ 530/327
See application file for complete search history.

(56) References Cited

U.S. PATENT DOCUMENTS

| | | | |
|---|---|---|---|
| 5,057,604 A | 10/1991 | Brown | 530/387 |
| 5,552,526 A | 9/1996 | Nakamura et al. | 530/350 |
| 5,574,136 A | 11/1996 | Nagata et al. | 530/350 |
| 5,919,656 A | 7/1999 | Harrington et al. | 435/69.1 |
| 5,922,561 A | 7/1999 | Thompson et al. | 435/69.1 |
| 5,994,072 A * | 11/1999 | Lam et al. | 435/6 |
| 6,031,076 A | 2/2000 | Falb et al. | 530/350 |
| 6,072,028 A | 6/2000 | Altieri | 530/324 |
| 6,174,682 B1 | 1/2001 | Khodadoust | 435/6 |
| 6,339,144 B1 | 1/2002 | Cigan et al. | 530/435 |
| 6,340,463 B1 | 1/2002 | Mitchell et al. | 424/263.1 |
| 6,358,721 B2 | 3/2002 | Patel | 435/194 |
| 6,358,923 B1 | 3/2002 | Yue et al. | 514/12 |
| 6,359,116 B1 | 3/2002 | Mathias | 530/350 |
| 6,365,371 B1 | 4/2002 | Tang et al. | 435/69.1 |
| 6,372,889 B1 | 4/2002 | Sheppard et al. | 530/350 |
| 6,372,890 B1 | 4/2002 | Koshida | 530/350 |
| 6,610,836 B1 * | 8/2003 | Breton et al. | 536/23.1 |
| 6,617,114 B1 * | 9/2003 | Fowlkes et al. | 435/7.1 |
| 6,747,137 B1 * | 6/2004 | Weinstock et al. | 536/23.1 |
| 2002/0165180 A1 | 11/2002 | Weaver | 514/44 |

OTHER PUBLICATIONS

Mawby et al. Isolation and characterization of CD47 glycoprotein: a multispanning membrane protein which is the same as integrin-associated protein (IAP) and the ovarian tumour marker OA3. Biochem J. Dec. 1, 1994;304 (Pt 2):525-30.*
Kuntz. Structure-based strategies for drug design and discovery. Science. 1992 257(5073):1078-1082.*
Miller et al Ligand binding to proteins: the binding landscape model. Protein Sci. Oct. 1997;6(10):2166-79.*
Attwood TK. Genomics. The Babel of bioinformatics. Science. 290(5491):471-473, 2000.*
Skolnick et al. From genes to protein structure and function: novel applications of computational approaches in the genomic era. Trends Biotechnol. 18(1):34-9, 2000.*
Jelokhani-Niaraki et al. Diastereoisomeric analogues of gramicidin S: structure, biologicalactivity and interaction with lipid bilayers. Biochem J. Aug. 1, 2000;349 Pt 3:747-55.*
Lerner RA. Tapping the immunological repertoire to produce antibodies of predetermined specificity. Nature. Oct. 14, 1982;299(5884):593-6..*
Subramanian et al. Phylogenetic divergence of CD47 interactions with human signal regulatory protein alpha reveals locus of species specificity. Implications for the binding site. J Biol Chem. Jan. 19, 2007;282(3):1805-18.*
Lu X et al., Preferential antagonism of the interactions of the integrin alpha IIb beta 3 with immobilized glycoprotein ligands by snake-venom RGD (Arg-Gly-Asp) proteins. Biochem J. Dec. 15, 1994;304 ( Pt 3):929-36.*
Yokoyama and Ramakrishnan Improved biological activity of a mutant endostatin containing a single amino-acid substitution.Br J Cancer. Apr. 19, 2004;90(8):1627-35.*
Aina et al. Therapeutic cancer targeting peptides. Biopolymers. 2002;66(3):184-99.*
Yuan Liu, et al.; Signal Regulatory Protein (SIRPα), a Cellular Ligand for CD47, Regulates Neutrophil Transmigration; The Journal of Biological Chemistry; vol. 227, No. 12, Mar. 22, 2002; pp. 10028-10036.
Liu et al.; Peptide-Mediated Inhibition of Neutrophil Transmigration by Blocking CD47 Interactions With Signal Regulatory Protein Alpha; J. Immunol.; Feb. 15, 2004, vol. 172, No. 4, pp. 2578-2585.

* cited by examiner

*Primary Examiner*—Maher M. Haddad
(74) *Attorney, Agent, or Firm*—Thomas, Kayden, Horstemeyer & Risley, LLP

(57) ABSTRACT

Polypeptides that can modulate SIRPα-CD47 functions and methods of use of the polypeptides are presented. In addition, polynucleotides that encode the polypeptides referred to above are presented. Further, pharmaceutical compositions to treat conditions are presented.

3 Claims, 10 Drawing Sheets

FIG. 1

SEQ ID NO:1 TGY GAR CGN GTN ATH GGN ACN GGN TAY GTN CGN TGY

SEQ ID NO:2 CERVIGTGWVRC

SEQ ID NO:3 TGY CGN CGN GTN ATH GGN CGN GTN GGN TGY GGN TGY

SEQ ID NO:4 CRRVIGRVGCGC

SEQ ID NO:5 TGY CAY CGN GTN CCN GGN CAY GGN TAY GTN CGN TGY

SEQ ID NO:6 CHRVPGHGWVRC

SEQ ID NO:7 TGY GGN TAY CGN AAY TCN TTY GGN CAR TCN CTN TGY

SEQ ID NO:8 CGWRNSFGQSLC

For SEQ ID NO:1, 3, 5, and 7 N is A, C,G or T

SEQ ID NO:9
    1 MWPLVAALLL GSACCGSAQL LFNKTKSVEF TFCNDTVVIP
CFVTNMEAQN TTEVYVKWKF 61 KGRDIYTFDG ALNKSTVPTD
FSSAKIEVSQ LLKGDASLKM DKSDAVSHTG NYTCEVTELT 121
REGETIIELK YRVVSWFSPN ENILIVIFPI FAILLFWGQF GIKTLKYRSG
GMDEKTIALL 181 VAGLVITVIV IVGAILFVPG EYSLKNATGL
GLIVTSTGIL ILLHYYVFST AIGLTSFVIA 241 ILVIQVIAYI LAVVGLSLCI
AACIPMHGPL LISGLSILAL AQLLGLVYMK FVASNQKTIQ 301 PPRNN

SEQ ID NO:46 CXRVXXXGWVRC
SEQ ID NO:47 CXR(VXX)[D/E/N/T]GW[V/C]R/(X)(X)(X)C
SEQ ID NO:48 CGWRNXXGQS[V/L]C
SEQ ID NO:49 C[R/X][E/D/T/G]GWC

Only one residue can reside between "[ ]", "/" means "or" so that those residues on either side of the "/" are interchangeable; residues in ( ) are either present or absent, X represents any variable residue

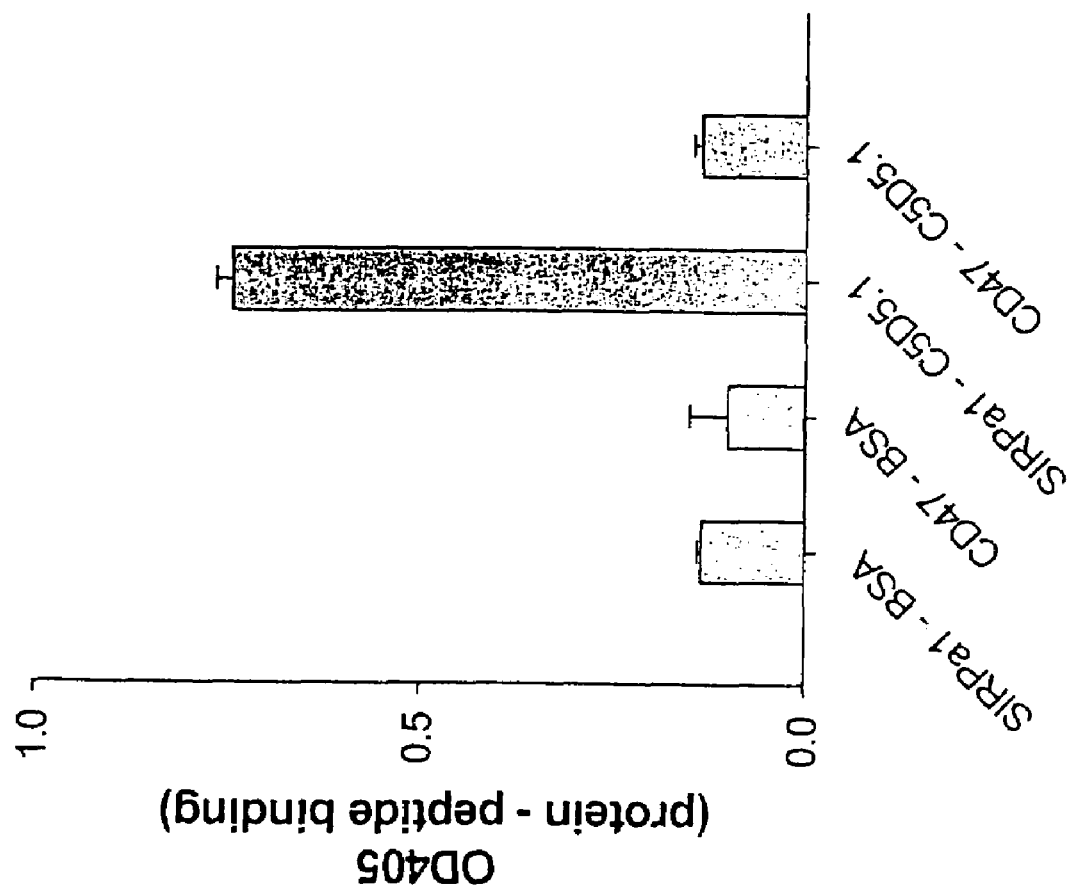

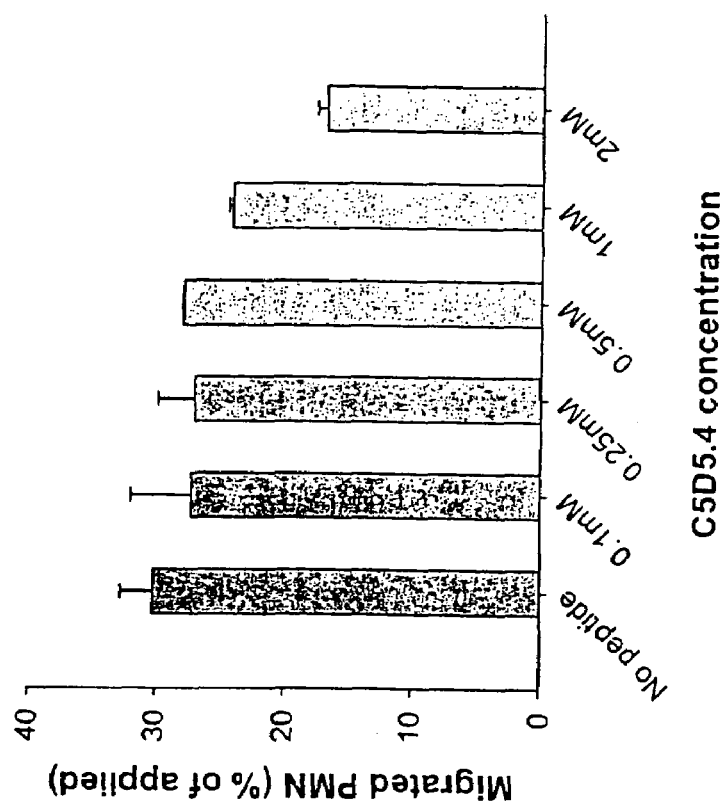
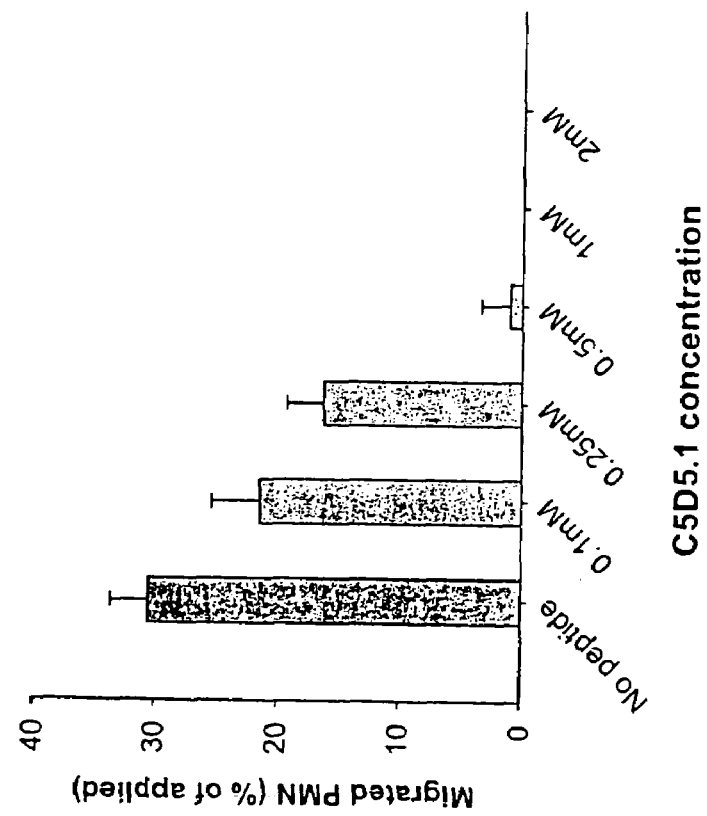

SEQUENCE LISTING

```
<160> NUMBER OF SEQ ID NOS: 49

<210> SEQ ID NO 1
<211> LENGTH: 36
<212> TYPE: DNA
<213> ORGANISM: Homo sapiens
<220> FEATURE:
<221> NAME/KEY: misc_feature
<222> LOCATION: (9)..(9)
<223> OTHER INFORMATION: Position 9 (N) represents A, C, G, or T
<220> FEATURE:
<221> NAME/KEY: misc_feature
<222> LOCATION: (12)..(12)
<223> OTHER INFORMATION: Position 12 (N) represents A, C, G, or T
<220> FEATURE:
<221> NAME/KEY: misc_feature
<222> LOCATION: (18)..(18)
<223> OTHER INFORMATION: Position 18 (N) represents A, C, G, or T
<220> FEATURE:
<221> NAME/KEY: misc_feature
<222> LOCATION: (21)..(21)
<223> OTHER INFORMATION: Position 21 (N) represents A, C, G, or T
<220> FEATURE:
<221> NAME/KEY: misc_feature
<222> LOCATION: (24)..(24)
<223> OTHER INFORMATION: Position 24 (N) represents A, C, G, or T
<220> FEATURE:
<221> NAME/KEY: misc_feature
<222> LOCATION: (30)..(30)
<223> OTHER INFORMATION: Position 30 (N) represents A, C, G, or T
<220> FEATURE:
<221> NAME/KEY: misc_feature
<222> LOCATION: (33)..(33)
<223> OTHER INFORMATION: Position 33 (N) represents A, C, G, or T

<400> SEQUENCE: 1
tgygarcgng tnathggnac nggntaygtn cgntgy                               36

<210> SEQ ID NO 2
<211> LENGTH: 12
<212> TYPE: PRT
<213> ORGANISM: Homo sapiens

<400> SEQUENCE: 2

Cys Glu Arg Val Ile Gly Thr Gly Trp Val Arg Cys
1               5                   10

<210> SEQ ID NO 3
<211> LENGTH: 36
<212> TYPE: DNA
<213> ORGANISM: Homo sapiens
<220> FEATURE:
<221> NAME/KEY: misc_feature
<222> LOCATION: (6)..(6)
<223> OTHER INFORMATION: Position 6 (N) represents A, C, G, or T
<220> FEATURE:
<221> NAME/KEY: misc_feature
<222> LOCATION: (9)..(9)
<223> OTHER INFORMATION: Position 9 (N) represents A, C, G, or T
<220> FEATURE:
<221> NAME/KEY: misc_feature
```

```
<222> LOCATION: (12)..(12)
<223> OTHER INFORMATION: Position12 (N) represents A, C, G, or T
<220> FEATURE:
<221> NAME/KEY: misc_feature
<222> LOCATION: (18)..(18)
<223> OTHER INFORMATION: Position18 (N) represents A, C, G, or T
<220> FEATURE:
<221> NAME/KEY: misc_feature
<222> LOCATION: (21)..(21)
<223> OTHER INFORMATION: Position 21 (N) represents A, C, G, or T
<220> FEATURE:
<221> NAME/KEY: misc_feature
<222> LOCATION: (24)..(24)
<223> OTHER INFORMATION: Position 24 (N) represents A, C, G, or T
<220> FEATURE:
<221> NAME/KEY: misc_feature
<222> LOCATION: (27)..(27)
<223> OTHER INFORMATION: Position 27 (N) represents A, C, G, or T
<220> FEATURE:
<221> NAME/KEY: misc_feature
<222> LOCATION: (33)..(33)
<223> OTHER INFORMATION: Position 33 (N) represents A, C, G, or T

<400> SEQUENCE: 3
tgycgncgng tnathggncg ngtnggntgy ggntgy                          36

<210> SEQ ID NO 4
<211> LENGTH: 12
<212> TYPE: PRT
<213> ORGANISM: Homo sapiens

<400> SEQUENCE: 4

Cys Arg Arg Val Ile Gly Arg Val Gly Cys Gly Cys
1               5                   10

<210> SEQ ID NO 5
<211> LENGTH: 36
<212> TYPE: DNA
<213> ORGANISM: Homo sapiens
<220> FEATURE:
<221> NAME/KEY: misc_feature
<222> LOCATION: (9)..(9)
<223> OTHER INFORMATION: Position 9 (N) represents A, C, G, or T
<220> FEATURE:
<221> NAME/KEY: misc_feature
<222> LOCATION: (12)..(12)
<223> OTHER INFORMATION: Position 12 (N) represents A, C, G, or T
<220> FEATURE:
<221> NAME/KEY: misc_feature
<222> LOCATION: (15)..(15)
<223> OTHER INFORMATION: Position 15 (N) represents A, C, G, or T
<220> FEATURE:
<221> NAME/KEY: misc_feature
<222> LOCATION: (18)..(18)
<223> OTHER INFORMATION: Position 18 (N) represents A, C, G, or T
<220> FEATURE:
<221> NAME/KEY: misc_feature
<222> LOCATION: (24)..(24)
<223> OTHER INFORMATION: Position 24 (N) represents A, C, G, or T
<220> FEATURE:
<221> NAME/KEY: misc_feature
<222> LOCATION: (30)..(30)
<223> OTHER INFORMATION: Position 30 (N) represents A, C, G, or T
<220> FEATURE:
<221> NAME/KEY: misc_feature
<222> LOCATION: (33)..(33)
<223> OTHER INFORMATION: Position 33 (N) represents A, C, G, or T

<400> SEQUENCE: 5
tgycaycgng tnccnggnca yggntaygtn cgntgy                          36

<210> SEQ ID NO 6
<211> LENGTH: 12
```

```
<212> TYPE: PRT
<213> ORGANISM: Homo sapiens

<400> SEQUENCE: 6

Cys His Arg Val Pro Gly His Gly Trp Val Arg Cys
1               5                   10

<210> SEQ ID NO 7
<211> LENGTH: 12
<212> TYPE: PRT
<213> ORGANISM: Homo sapiens

<400> SEQUENCE: 7

Cys Gly Trp Arg Asn Ser Phe Gly Gln Ser Leu Cys
1               5                   10

<210> SEQ ID NO 8
<211> LENGTH: 305
<212> TYPE: PRT
<213> ORGANISM: Homo sapiens

<400> SEQUENCE: 8

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
```

```
                275                 280                 285
Met Lys Phe Val Ala Ser Asn Gln Lys Thr Ile Gln Pro Pro Arg Asn
    290                 295                 300

Asn
305

<210> SEQ ID NO 9
<211> LENGTH: 12
<212> TYPE: PRT
<213> ORGANISM: Homo sapiens

<400> SEQUENCE: 9

Cys Ser Trp Gln His Gln Asp Gly Trp Val Trp Cys
1               5                   10

<210> SEQ ID NO 10
<211> LENGTH: 12
<212> TYPE: PRT
<213> ORGANISM: Homo sapiens

<400> SEQUENCE: 10

Cys Val Pro Val Cys Arg Glu Gly Trp Cys Gly Cys
1               5                   10

<210> SEQ ID NO 11
<211> LENGTH: 12
<212> TYPE: PRT
<213> ORGANISM: Homo sapiens

<400> SEQUENCE: 11

Cys Tyr Lys Ser Met Asp Gly Trp Val Val Pro Cys
1               5                   10

<210> SEQ ID NO 12
<211> LENGTH: 12
<212> TYPE: PRT
<213> ORGANISM: Homo sapiens

<400> SEQUENCE: 12

Cys Val Glu Asn Val Asp Gly Trp Thr Val Pro Cys
1               5                   10

<210> SEQ ID NO 13
<211> LENGTH: 11
<212> TYPE: PRT
<213> ORGANISM: Homo sapiens

<400> SEQUENCE: 13

Cys Arg Val Pro Glu Thr Gly Trp Val Lys Cys
1               5                   10

<210> SEQ ID NO 14
<211> LENGTH: 12
<212> TYPE: PRT
<213> ORGANISM: Homo sapiens

<400> SEQUENCE: 14

Cys Arg Leu Met Leu Asn Gly Trp Val Val Pro Cys
1               5                   10

<210> SEQ ID NO 15
<211> LENGTH: 12
<212> TYPE: PRT
<213> ORGANISM: Homo sapiens
```

```
<400> SEQUENCE: 15

Cys Cys Arg Asp Gly Trp Cys His His Asp Trp Cys
1               5                   10

<210> SEQ ID NO 16
<211> LENGTH: 12
<212> TYPE: PRT
<213> ORGANISM: Homo sapiens

<400> SEQUENCE: 16

Cys Cys Arg Glu Gly Trp Cys Gly Asp Gly Leu Cys
1               5                   10

<210> SEQ ID NO 17
<211> LENGTH: 12
<212> TYPE: PRT
<213> ORGANISM: Homo sapiens

<400> SEQUENCE: 17

Cys Gly Trp Arg Asn Ala Leu Gly Gln Val Val Cys
1               5                   10

<210> SEQ ID NO 18
<211> LENGTH: 12
<212> TYPE: PRT
<213> ORGANISM: Homo sapiens

<400> SEQUENCE: 18

Cys Gly Trp Arg Asn Leu Glu Gly Gly Ser Val Cys
1               5                   10

<210> SEQ ID NO 19
<211> LENGTH: 12
<212> TYPE: PRT
<213> ORGANISM: Homo sapiens

<400> SEQUENCE: 19

Cys Gly Trp Arg Asp Asp Ser Gly Gln Ser Met Cys
1               5                   10

<210> SEQ ID NO 20
<211> LENGTH: 7
<212> TYPE: PRT
<213> ORGANISM: Homo sapiens

<400> SEQUENCE: 20

Trp Cys Arg Gly Gly Trp Cys
1               5

<210> SEQ ID NO 21
<211> LENGTH: 7
<212> TYPE: PRT
<213> ORGANISM: Homo sapiens

<400> SEQUENCE: 21

Trp Cys Lys Ser Gly Trp Cys
1               5

<210> SEQ ID NO 22
<211> LENGTH: 8
<212> TYPE: PRT
<213> ORGANISM: Homo sapiens

<400> SEQUENCE: 22
```

```
Cys Leu Cys Ala Glu Gly Trp Cys
1               5

<210> SEQ ID NO 23
<211> LENGTH: 8
<212> TYPE: PRT
<213> ORGANISM: Homo sapiens

<400> SEQUENCE: 23

Cys His Pro Gly Thr Gly Trp Cys
1               5

<210> SEQ ID NO 24
<211> LENGTH: 8
<212> TYPE: PRT
<213> ORGANISM: Homo sapiens

<400> SEQUENCE: 24

Ser Tyr Cys Arg Glu Gly Trp Cys
1               5

<210> SEQ ID NO 25
<211> LENGTH: 8
<212> TYPE: PRT
<213> ORGANISM: Homo sapiens

<400> SEQUENCE: 25

Cys Gly Cys Arg Asp Gly Trp Cys
1               5

<210> SEQ ID NO 26
<211> LENGTH: 8
<212> TYPE: PRT
<213> ORGANISM: Homo sapiens

<400> SEQUENCE: 26

Cys Leu Cys His Gly Gly Trp Cys
1               5

<210> SEQ ID NO 27
<211> LENGTH: 7
<212> TYPE: PRT
<213> ORGANISM: Homo sapiens

<400> SEQUENCE: 27

Trp Cys Val Lys Gly Trp Cys
1               5

<210> SEQ ID NO 28
<211> LENGTH: 8
<212> TYPE: PRT
<213> ORGANISM: Homo sapiens

<400> SEQUENCE: 28

Cys Arg Asp Gly Trp Cys Tyr Ser
1               5

<210> SEQ ID NO 29
<211> LENGTH: 8
<212> TYPE: PRT
<213> ORGANISM: Homo sapiens

<400> SEQUENCE: 29

Cys Val Ala Ile Leu Lys Asp Cys
```

```
<210> SEQ ID NO 30
<211> LENGTH: 9
<212> TYPE: PRT
<213> ORGANISM: Homo sapiens

<400> SEQUENCE: 30

Gly Trp Pro Arg Val Gly Phe Arg Leu
1               5

<210> SEQ ID NO 31
<211> LENGTH: 9
<212> TYPE: PRT
<213> ORGANISM: Homo sapiens

<400> SEQUENCE: 31

Gly Leu Val Lys Asp Ala Gly Phe Phe
1               5

<210> SEQ ID NO 32
<211> LENGTH: 0
<212> TYPE: DNA
<213> ORGANISM: Homo sapiens

<400> SEQUENCE: 32

000

<210> SEQ ID NO 33
<211> LENGTH: 10
<212> TYPE: PRT
<213> ORGANISM: Homo sapiens

<400> SEQUENCE: 33

Glu Arg Val Ile Gly Thr Gly Trp Val Arg
1               5                   10

<210> SEQ ID NO 34
<211> LENGTH: 12
<212> TYPE: PRT
<213> ORGANISM: Homo sapiens

<400> SEQUENCE: 34

Cys Gly Val Arg Thr Trp Arg Gly Val Ile Glu Cys
1               5                   10

<210> SEQ ID NO 35
<211> LENGTH: 12
<212> TYPE: PRT
<213> ORGANISM: Homo sapiens

<400> SEQUENCE: 35

Cys His Arg Val Ile Gly Thr Gly Trp Val Arg Cys
1               5                   10

<210> SEQ ID NO 36
<211> LENGTH: 6
<212> TYPE: PRT
<213> ORGANISM: Homo sapiens

<400> SEQUENCE: 36

Cys Arg Asp Gly Trp Cys
1               5
```

```
<210> SEQ ID NO 37
<211> LENGTH: 6
<212> TYPE: PRT
<213> ORGANISM: Homo sapiens

<400> SEQUENCE: 37

Cys Arg Glu Gly Trp Cys
1               5

<210> SEQ ID NO 38
<211> LENGTH: 35
<212> TYPE: DNA
<213> ORGANISM: Homo sapiens

<400> SEQUENCE: 38
ggaatgccgt ggttggtgcg gacctcctac tgttg                           35

<210> SEQ ID NO 39
<211> LENGTH: 44
<212> TYPE: DNA
<213> ORGANISM: Homo sapiens

<400> SEQUENCE: 39
ctagcaacag taggaggtcc gcaccaacca tcccggcatt ccgc                 44

<210> SEQ ID NO 40
<211> LENGTH: 38
<212> TYPE: DNA
<213> ORGANISM: Homo sapiens

<400> SEQUENCE: 40
ggaatgccgg gagggttggt gcggacctcc tactgttg                        38

<210> SEQ ID NO 41
<211> LENGTH: 47
<212> TYPE: DNA
<213> ORGANISM: Homo sapiens

<400> SEQUENCE: 41
ggaatgcggt tggcgtaatg gtcagtcttg cggacctcct actgttg              47

<210> SEQ ID NO 42
<211> LENGTH: 21
<212> TYPE: DNA
<213> ORGANISM: Homo sapiens

<400> SEQUENCE: 42
gcagaccttt ctgctgtttt g                                          21

<210> SEQ ID NO 43
<211> LENGTH: 35
<212> TYPE: DNA
<213> ORGANISM: Homo sapiens

<400> SEQUENCE: 43
atgataagct tcctgcatgt ggcccctggt agcgg                           35

<210> SEQ ID NO 44
<211> LENGTH: 30
<212> TYPE: DNA
<213> ORGANISM: Homo sapiens

<400> SEQUENCE: 44
ttgattagat ctatttggag aaaaccatga                                 30
```

```
<210> SEQ ID NO 45
<211> LENGTH: 12
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Position 2 represents a variable residue
<220> FEATURE:
<221> NAME/KEY: MISC_FEATURE
<222> LOCATION: (5)..(5)
<223> OTHER INFORMATION: Position 5 represents a variable residue
<220> FEATURE:
<221> NAME/KEY: MISC_FEATURE
<222> LOCATION: (6)..(6)
<223> OTHER INFORMATION: Position 6 represents a variable residue
<220> FEATURE:
<221> NAME/KEY: MISC_FEATURE
<222> LOCATION: (7)..(7)
<223> OTHER INFORMATION: Position 7 represents a variable residue

<400> SEQUENCE: 45

Cys Xaa Arg Val Xaa Xaa Xaa Gly Trp Val Arg Cys
1               5                   10

<210> SEQ ID NO 46
<211> LENGTH: 36
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Position 2 represents a variable residue
<220> FEATURE:
<221> NAME/KEY: MISC_FEATURE
<222> LOCATION: (6)..(6)
<223> OTHER INFORMATION: Position 6 represents a variable residue
<220> FEATURE:
<221> NAME/KEY: MISC_FEATURE
<222> LOCATION: (7)..(7)
<223> OTHER INFORMATION: Position 7 represents a variable residue
<220> FEATURE:
<221> NAME/KEY: MISC_FEATURE
<222> LOCATION: (28)..(28)
<223> OTHER INFORMATION: Position 28 represents a variable residue
<220> FEATURE:
<221> NAME/KEY: MISC_FEATURE
<222> LOCATION: (31)..(31)
<223> OTHER INFORMATION: Position 31 represents a variable residue
<220> FEATURE:
<221> NAME/KEY: MISC_FEATURE
<222> LOCATION: (34)..(34)
<223> OTHER INFORMATION: Position 34 represents a variable residue
<220> FEATURE:
<221> NAME/KEY: MISC_FEATURE
<222> LOCATION: (4)..(4)
<223> OTHER INFORMATION: Position 4 represents an open parenthesis;
                        residues in () are either present or absent; X
                        represents any variable residue
<220> FEATURE:
<221> NAME/KEY: MISC_FEATURE
<222> LOCATION: (27)..(27)
<223> OTHER INFORMATION: Position 27 represents an open parenthesis;
                        residues in () are either present or absent; X
                        represents any variable residue
<220> FEATURE:
<221> NAME/KEY: MISC_FEATURE
<222> LOCATION: (30)..(30)
<223> OTHER INFORMATION: Position 30 represents an open parenthesis;
                        residues in () are either present or absent; X
                        represents any variable residue
<220> FEATURE:
<221> NAME/KEY: MISC_FEATURE
<222> LOCATION: (33)..(33)
<223> OTHER INFORMATION: Position 33 represents an open parenthesis;
```

```
                    residues in () are either present or absent; X
                    represents any variable residue
<220> FEATURE:
<221> NAME/KEY: MISC_FEATURE
<222> LOCATION: (8)..(8)
<223> OTHER INFORMATION: Position 8 represents a closed parenthesis;
                    residues in () are either present or absent; X
                    represents any variable residue
<220> FEATURE:
<221> NAME/KEY: MISC_FEATURE
<222> LOCATION: (29)..(29)
<223> OTHER INFORMATION: Position 29 represents a closed parenthesis;
                    residues in () are either present or absent; X
                    represents any variable residue
<220> FEATURE:
<221> NAME/KEY: MISC_FEATURE
<222> LOCATION: (32)..(32)
<223> OTHER INFORMATION: Position 32 represents a closed parenthesis;
                    residues in () are either present or absent; X
                    represents any variable residue
<220> FEATURE:
<221> NAME/KEY: MISC_FEATURE
<222> LOCATION: (35)..(35)
<223> OTHER INFORMATION: Position 35 represents a closed parenthesis;
                    residues in () are either present or absent; X
                    represents any variable residue
<220> FEATURE:
<221> NAME/KEY: MISC_FEATURE
<222> LOCATION: (9)..(9)
<223> OTHER INFORMATION: Position 9 represents an open bracket; only
                    one residue can reside between  brackets <220> FEATURE:
<221> NAME/KEY: MISC_FEATURE
<222> LOCATION: (20)..(20)
<223> OTHER INFORMATION: Position 20 represents an open bracket; only
                    one residue can reside between  brackets <220> FEATURE:
<221> NAME/KEY: MISC_FEATURE
<222> LOCATION: (17)..(17)
<223> OTHER INFORMATION: Position17 represents a closed bracket; only
                    one residue can reside between  brackets <220> FEATURE:
<221> NAME/KEY: MISC_FEATURE
<222> LOCATION: (24)..(24)
<223> OTHER INFORMATION: Position 24 represents a closed bracket; only
                    one residue can reside between  brackets
<220> FEATURE:
<221> NAME/KEY: MISC_FEATURE
<222> LOCATION: (11)..(11)
<223> OTHER INFORMATION: Position 11 represents a slash; "/" means "or"
                    so that those residues on either side of the
                    "/" are interchangeable
<220> FEATURE:
<221> NAME/KEY: MISC_FEATURE
<222> LOCATION: (13)..(13)
<223> OTHER INFORMATION: Position 13 represents a slash; "/" means "or"
                    so that those residues on either side of the
                    "/" are interchangeable
<220> FEATURE:
<221> NAME/KEY: MISC_FEATURE
<222> LOCATION: (15)..(15)
<223> OTHER INFORMATION: Position 15 represents a slash; "/" means "or"
                    so that those residues on either side of the
                    "/" are interchangeable
<220> FEATURE:
<221> NAME/KEY: MISC_FEATURE
<222> LOCATION: (22)..(22)
<223> OTHER INFORMATION: Position 22 represents a slash; "/" means "or"
                    so that those residues on either side of the
                    "/" are interchangeable
<220> FEATURE:
<221> NAME/KEY: MISC_FEATURE
<222> LOCATION: (26)..(26)
<223> OTHER INFORMATION: Position 26 represents a slash; "/" means "or"
                    so that those residues on either side of the
                    "/" are interchangeable
```

<400> SEQUENCE: 46

Cys Xaa Arg Xaa Val Xaa Xaa Xaa Xaa Asp Xaa Glu Xaa Asn Xaa Thr
1               5                   10                  15
Xaa Gly Trp Xaa Val Xaa Cys Xaa Arg Xaa Xaa Xaa Xaa Xaa Xaa
            20                  25                  30
Xaa Xaa Xaa Cys
        35

<210> SEQ ID NO 47
<211> LENGTH: 16
<212> TYPE: PRT
<213> ORGANISM: Homo sapiens
<220> FEATURE:
<221> NAME/KEY: MISC_FEATURE
<222> LOCATION: (6)..(7)
<223> OTHER INFORMATION: Positions 6 and 7 represent a variable residue
<220> FEATURE:
<221> NAME/KEY: MISC_FEATURE
<222> LOCATION: (11)..(11)
<223> OTHER INFORMATION: Position 11 represents an open bracket; only
                  one residue can reside between brackets
<220> FEATURE:
<221> NAME/KEY: MISC_FEATURE
<222> LOCATION: (15)..(15)
<223> OTHER INFORMATION: Position 15 represents a closed bracket; only
                  one residue can reside between brackets
<220> FEATURE:
<221> NAME/KEY: MISC_FEATURE
<222> LOCATION: (13)..(13)
<223> OTHER INFORMATION: Position 13 represents a slash; "/" means "or"
                  so that those residues on either side of the
                  "/" are interchangeable

<400> SEQUENCE: 47

Cys Gly Trp Arg Asn Xaa Xaa Gly Gln Ser Xaa Val Xaa Leu Xaa Cys
1               5                   10                  15

<210> SEQ ID NO 48
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Position 2 represents an open bracket; only one
                  residue can reside between brackets
<220> FEATURE:
<221> NAME/KEY: MISC_FEATURE
<222> LOCATION: (7)..(7)
<223> OTHER INFORMATION: Position 7 represents an open bracket; only one
                  residue can reside between brackets
<220> FEATURE:
<221> NAME/KEY: MISC_FEATURE
<222> LOCATION: (6)..(6)
<223> OTHER INFORMATION: Position 6 represents a closed bracket; only
                  one residue can reside between brackets
<220> FEATURE:
<221> NAME/KEY: MISC_FEATURE
<222> LOCATION: (15)..(15)
<223> OTHER INFORMATION: Position 15 represents a closed bracket; only
                  one residue can reside between brackets
<220> FEATURE:
<221> NAME/KEY: MISC_FEATURE
<222> LOCATION: (4)..(4)
<223> OTHER INFORMATION: Position 4 represents a slash: "/" means "or"
                  so that those residues on either side of the
                  "/" are interchageable
<220> FEATURE:
<221> NAME/KEY: MISC_FEATURE
<222> LOCATION: (9)..(9)
<223> OTHER INFORMATION: Position 9 represents a slash: "/" means "or"
                  so that those residues on either side of the
                  "/" are interchageable
<220> FEATURE:

```
<221> NAME/KEY: MISC_FEATURE
<222> LOCATION: (11)..(11)
<223> OTHER INFORMATION: Position 11 represents a slash: "/" means "or"
                        so that those residues on either side of the
                        "/" are interchageable
<220> FEATURE:
<221> NAME/KEY: MISC_FEATURE
<222> LOCATION: (13)..(13)
<223> OTHER INFORMATION: Position 13 represents a slash: "/" means "or"
                        so that those residues on either side of the
                        "/" are interchageable
<220> FEATURE:
<221> NAME/KEY: MISC_FEATURE
<222> LOCATION: (5)..(5)
<223> OTHER INFORMATION: Position 5 represents a variable residue

<400> SEQUENCE: 48

Cys Xaa Arg Xaa Xaa Xaa Xaa Glu Xaa Asp Xaa Thr Xaa Gly Xaa Gly
1               5                   10                  15

Trp Cys

<210> SEQ ID NO 49
<211> LENGTH: 36
<212> TYPE: DNA
<213> ORGANISM: Homo sapiens
<220> FEATURE:
<221> NAME/KEY: misc_feature
<222> LOCATION: (6)..(6)
<223> OTHER INFORMATION: Position 6 (N) represents A, C, G or T
<220> FEATURE:
<221> NAME/KEY: misc_feature
<222> LOCATION: (12)..(12)
<223> OTHER INFORMATION: Position 12 (N) represents A, C, G or T
<220> FEATURE:
<221> NAME/KEY: misc_feature
<222> LOCATION: (18)..(18)
<223> OTHER INFORMATION: Position 18 (N) represents A, C, G or T
<220> FEATURE:
<221> NAME/KEY: misc_feature
<222> LOCATION: (24)..(24)
<223> OTHER INFORMATION: Position 24 (N) represents A, C, G or T
<220> FEATURE:
<221> NAME/KEY: misc_feature
<222> LOCATION: (30)..(30)
<223> OTHER INFORMATION: Position 30 (N) represents A, C, G or T
<220> FEATURE:
<221> NAME/KEY: misc_feature
<222> LOCATION: (33)..(33)
<223> OTHER INFORMATION: Position 33 (N) represents A, C, G or T

<400> SEQUENCE: 49
tgyggntayc gnaaytcntt yggncartcn ctntgy                              36
```

POLYNUCLEOTIDES AND POLYPEPTIDES RELATING TO THE MODULATION OF SIRPα-CD47

CROSS-REFERENCE TO RELATED APPLICATION

This application claims priority to U.S. provisional application entitled, "Peptides That Modulate SIRP-CD47 Function," having Ser. No. 60/291050, filed May 15, 2001, which is entirely incorporated herein by reference.

STATEMENT REGARDING FEDERALLY SPONSORED RESEARCH OR DEVELOPMENT

The U.S. government has a paid-up license in this invention and the right in limited circumstances to require the patent owner to license others on reasonable terms as provided for by the terms of Grant No.: HL60540 awarded by the National Institute of Health.

TECHNICAL FIELD

The present invention is generally related to polynucleotides and polypeptides and, more particularly, is related to polynucleotides and polypeptides relating to the modulation of SIRPα-CD47 interactions.

BACKGROUND

A variety of human diseases, in their active stages, are characterized by migration of large numbers of neutrophils (PMN) through tissues and across mucosal surfaces. For example, in inflammatory pulmonary diseases, such as bronchitis, cystic fibrosis and bronchiectasis, acute inflammation of the airway is characterized by infiltration of bronchial epithelium with neutrophils. In the urinary system, migration of PMN across tubular and transitional epithelium is associated with cystitis and pyelonephritis. In the gastrointestinal tract, active inflammatory disease characterized by migration of PMN across the epithelial lining is the hallmark of chronic and self-limited diseases such as ulcerative colitis, Crohn's disease and bacterial eriterocolitis. In these conditions, epithelial injury, disease activity and symptoms parallel PMN infiltration of the mucosa. (Hawker, et al., *Gastroenterology*, 79: 508, 1980; Weiland, et al., *Am. Rev. Respir. Dis.*, 133: 218, 1986; Nusrat, et al., *Gastroenterology*, 113: 1489, 1997; Koyama, et al., *Immunol.*, 147: 4293, 1991).

The emigration of circulating PMN from the blood stream to mucosal surfaces is an essential component of the acute inflammatory response and involves a complex and incompletely understood series of events. During this process, there are sequential, bi-directional interactions of PMN with endothelial cells, interstitial matrix and, under many conditions, epithelial cells. During the initial phases of recruitment, circulating PMN are activated by exposure to inflammatory mediators including complement fragments, cytokines such as IL-8 and tumor necrosis factor, and lipopolysaccharide leading to their microvascular sequestration and firm adhesion to the endothelium (Pober, et al., *Transplantation*, 50: 537, 1990; Luscinskas, et al., *J. Immunol.*, 146: 1617, 1991; Smith, et al., *J. Immunology*, 72: 65, 1991). Sequestered PMN then migrate across the vascular endothelium, a process that involves sequential interactions between PMN integrins and endothelial cell adhesion molecules including ICAM and PECAM (Smith, et al., *Semin. Hematol.*, 30:45, 1993; Smith, et al., *J. Clin. Invest.*, 83: 2008, 1990; Springer, *Nature*, 346: 425, 1990; Muller, et al., *J. Exp. Med.*, 178: 449, 1993). In the extravascular space, directed PMN migration depends on the presence of a chemotactic stimulus and interactions between extracellular matrix proteins and adhesion molecules. Chemotactic stimuli can be produced locally by activated cells or by external pathogens. For example, intestinal epithelial cells secrete the chemoattractant IL-8 in a basolaterally polarized manner as a response to many pathogens (McCormick, et al., *J. Cell Biol.*, 131: 1599, 1995) which then serves to recruit PMN from the circulation to the sub-epithelial space. PMN migration across the epithelium is then directed towards bacterial-derived peptides such as fMLF and requires sequential adhesive and signaling interactions along the basolateral epithelial cell membrane (Parkos, *Bioessays*, 19: 865, 1997).

While many of the molecular steps involved in this complex process of transmigration are still undefined, it has been demonstrated that a transmembrane protein termed CD47 plays an important role in regulating PMN migration at the level of the endothelium, matrix and epithelium (Parkos, et al., *J. Cell Biol.*, 132: 437, 1996; Cooper, et al., *Proc Natl Acad Sci USA*, 92: 3978, 1995). In particular, it has been shown that CD47 is a crucial component of the transepithelial migration response and that CD47-dependent events occur after $\beta_2$ integrin-mediated neutrophil adhesion to the epithelium (Parkos, et al., *J. Cell Biol.*, 132: 437, 1996). Recently it was reported that CD47 binds to another class of transmembrane Ig superfamily members called Signal Regulatory Proteins (SIRPs) (Jiang, et al., *J. Biol. Chem.*, 274: 559, 1999; Seiffert, et al., *Blood*, 94: 3633, 1999). SIRP's have been implicated in both positive and negative signal transduction cascades in a variety of cell types. CD47 was first purified from human placenta in 1990 (Brown, et al., *J. Cell Biol.*, 111: 2785, 1990), and the complete cDNA sequence was reported by Campbell (Campbell, et al., *Cancer Res*, 52: 5416, 1992) and Lindberg et al. (Lindberg, et al., *J. Cell Biol*, 123: 485, 1993) and is widely expressed in hematopoietic cells (e.g., erythrocytes, lymphocytes, platelets, monocytes and neutrophils) and other tissues (e.g., placenta, surface epithelia, liver and brain). The human CD47 gene has been mapped to chromosome 3, band q 13.1-q 13.2 and encodes a protein of 305 amino acids (isoform 2) with a predicted core polypeptide molecular weight of 35 kDa and four isoforms have been cloned and characterized (Campbell, et al., *Cancer Res*, 52: 5416, 1992; Lindberg, et al., *J. Cell Biol.*, 123: 485, 1993; Reinhold, et al., *Journal of Experimental Medicine*, 185: 119-21, 1997). The primary sequence of CD47 predicts an N terminal extracellular domain that structurally belongs to the immunoglobulin variable-like (IgV) superfamily (Lindberg, et al., *J. Cell Biol.*, 123: 485, 1996; Vaughn, et al., *Neuron* 16(2): 261-73, 1996) containing a disulfide bridge harboring several potential N-glycosylation sites. Several hydrophobic helices suggest three or five transmembrane segments. There is a short hydrophilic intracytoplasmic tail with four alternatively spliced forms that are expressed in a tissue-specific manner (Campbell, et al., *Cancer Res*, 52: 5416, 1992; Lindberg, et al., *J. Cell Biol.*, 123: 485, 1993; Reinhold, et al., *Journal of Experimental Medicine*, 185: 1, 1997). Studies with several IgV superfamily proteins have shown that the IgV-like domain is important in cell surface adhesive functions (Vaughn, et al., *Neuron* 16(2): 261-73, 1996). Studies using depletion and chimeric constructs suggest that the extracellular IgV-like domain of CD47 is important for its ability to regulate $\beta_3$ integrin avidity for immobilized vitronectin (Lindberg, et al., *J. Cell Biol.*, 123: 485, 1996). Direct association between CD47 and $\beta_3$ integrin was first demonstrated by coimmunoprecipitation experiments in placenta (Brown, et al., *J. Cell Biol.*, 111: 2785, 1990). These findings have further been validated by studies using CD47 knock out mice who rapidly die of *Escherichia coli* peritonitis, a phenomenon directly correlated with a reduction in leukocyte activation in response to $\beta_3$ integrin ligation (Lindberg, et al., *J. Cell Biol.*, 123: 485, 1996).

CD47 has been shown to have a central role in PMN transepithelial migration (Parkos, et al., *J. Cell Biol.*, 132: 437, 1996). A potent CD47-specific antibody (Ab), C5/D5, was identified that was capable of inhibiting PMN migration across vascular endothelium, collagen-coated filters and intestinal epithelium without inhibiting $\beta_2$ integrin-mediated adhesion (Parkos, et al., *J. Cell Biol.*, 132: 437, 1996). At the same time, it was shown that anti-CD47 also inhibited PMN migration across endothelial monolayers (Cooper, et al., *Proc Natl Acad Sci USA*, 92: 3978, 1995). Subsequent studies with CD47 knockout mice have confirmed the importance of CD47 in PMN migration in vivo suggesting that CD47 plays a role in regulating the rate of PMN recruitment to sites of infection. (Lindberg, et al., *Science*, 274: 795, 1996)

Despite a growing number of reports of different functions of CD47 (Parkos, et al., *J. Cell Biol.*, 132: 437, 1996; Jiang, et al., *J. Cell Biol.*, 274: 559, 1999; Lindberg, et al., *J. Cell Biol.*, 134: 1313, 1996; Ticchioni, et al., *Journal of Immunology*, 158: 677, 1997; Waclavicek, et al., *Journal of Immunology*, 159: 5345, 1997; Gao, et al., *J. Cell Biol.*, 135: 533, 1996; Furusawa, et al., *J. Biol. Chem.*, 123: 101, 1998; Frazier, et al., *J. Biol. Chem.*, 274: 8554, 1999; Chung, et al., *J. Biol. Chem.*, 272: 14740, 1997; Chung, et al., *Blood*, 94: 642, 1999), the mechanism by which CD47 regulates PAN migration is not known. In other cell systems, CD47 has been shown to functionally and physically associate with $\beta_3$ and $\beta_1$ integrins (Brown, et al., *J. Cell Biol.*, 111: 2785, 1990; Lindberg, et al., *J. Cell Biol.*, 134:1313, 1996; Frazier, et al., *J. Biol. Chem.*, 274: 8554, 1999; Blystone, et al., *J. Cell Biol.*, 130: 745, 1995; Lindberg, et al., *J. Cell Biol.*, 123: 485, 1996). However, others have not been able to detect a direct association of CD47 with $\beta_1$, $\beta_2$, and $\beta_3$ integrins in PMN and observe no significant effect on PMN transepithelial migration in the presence of a panel of functionally inhibitory mAbs against $\beta_3$ integrin or $\beta_1$ integrin (Liu, et al., *J. Biol. Chem.*, 276: 40156). CD47 has also been shown to bind to the C-terminal cell binding domain of thrombospondin1 (Gao, et al., *J. Biol. Chem.*, 271: 21, 1996), but this interaction does not modulate PMN migration (Liu, et al., *J. Biol. Chem.*, 276: 40156, 2001). Recent in vitro studies have suggested that CD47 regulates the rate of PMN migration (Liu, et al., *J. Biol. Chem.*, 276: 40156, 2001). In that study it was found that anti-CD47 mAbs delayed PMN migration across both T84 epithelial monolayers and matrix-coated permeable filters towards the chemoattractant fMLF. However, despite delayed transmigration, the numbers of PMN migrating across were not affected by the presence of anti-CD47 antibodies. This finding is consistent with studies with CD47 knock-out mice (Lindberg, et al., *Science*, 274: 795, 1996) suggesting that, although CD47 deficient PMN can eventually migrate to sites of infection, the delayed response resulted in enhanced mortality.

As indicated above, surface Ig superfamily member SIRPα (also termed SIRPα1; P84, Bit, SHPS-1 and MFR) (Jiang, et al., *J. Biol. Chem.*, 274: 559, 1999; Seiffert, et al., *Blood*, 94: 3633, 1999; Vernon-Wilson, et al., *European Journal of Immunology*, 30: 2130, 2000; Kharitonenkov, et al., *Nature*, 386: 181, 1997; Han, et al., *J. Biol. Chem.*, 275: 3798, 2000; Brumell, et al., *J. Biol. Chem.*, 272: 875, 1997) was reported to bind to CD47. SIRPs are a family of transmembrane glycoproteins expressed in a variety of tissues (Kharitonenkov, et al., *Nature*, 386: 181, 1997). However, within these tissues, SIRPs are only selectively expressed in certain cell types (Adams, et al., *Journal of Immunology*, 161: 1853, 1998). In mice, SIRPs (termed SHPS-1) are richly expressed in hematopoietic cells including macrophages and myeloid cells, but not in T and B cells (Veillette, et al., *J. Biol. Chem.*, 273: 22719, 1998). In humans, SIRPs are expressed in monocytes, granulocytes, dendritic cells and CD34+CD38−CD133+bone marrow stem/progenitor cells but not in lymphocytes (Seiffert, et al., *Blood*, 94: 3633, 1999; Seiffert, et al., *Blood*, 97: 2741, 2001). Through cDNA library screening, multiple homologous sequences that account for at least 15 additional SIRP members have been reported (Kharitonenkov, et al., *Nature*, 386: 181, 1997).

Primary structural analysis indicates that SIRPs all share common structural motifs that comprise a single transmembrane segment and an N-terminal extracellular domain that contains three Ig-like loops connected by three pairs of disulfide bonds. Therefore, SIRPs structurally belong to the Ig superfamily. The C-terminal intracellular domain, on the other hand, structurally separates two subfamilies of SIRPs termed SIRPα and SIRPβ (Kharitonenkov, et al., *Nature*, 386: 181, 1997). SIRPα has a long intracellular domain containing four tyrosine residues that form two immunoreceptor tyrosine-based inhibitory motifs (ITIM), while SIRPβ contains a basic lysine residue followed by a short intracellular tail that serves as a receptor for DAP12, a protein with an immunoreceptor tyrosine-based activation motif (Kharitonenkov, et al., *Nature*, 386: 181, 1997; Seiffert, et al., *Blood*, 97: 2741, 2001).

Similar to other ITIM domain containing proteins such as CD3, TCRξ, FcRγ, and BCR (Tomasello, et al., *Seminars in Immunology*, 12: 139, 2000; Vivier, et al., *Immunology Today*, 18: 286, 1997), SIRPα has been shown to play an important role in regulating cellular responses to a wide variety of different stimuli. For example, treatment of tissue-cultured cells with growth factors (including PDGF and EGF), growth hormone, insulin, CSF, LPA, etc., has been shown to induce phosphorylation of tyrosines on the intracellular ITINI domain of SIRPα resulting in binding to SH2 domain containing tyrosine phosphatase-1 or 2 (SHP-1 and 2) (Kharitonenkov, et al., *Nature*, 386:181, 1997; Veillette, et al., *J. Biol. Chem.*, 273: 22719, 1998; Timms, et al., *Molecular & Cellular Biology*, 18: 3838, 1998). SIRPα binding to SHP-1 or SHP-2 has been shown to deliver positive or negative signals that regulate a variety of cellular functions, respectively (Kharitonenkov, et al., *Nature*, 386:181, 1997; Stofega, et al., *J. Biol. Chem.*, 275: 28222, 2000; Stofega, et al., *J. Biol. Chem.*, 273: 7112, 1998).

As mentioned above, there are recent reports of SIRPα1 as an extracellular ligand for CD47. These findings are important in that no membrane protein receptor has been described for either SIRP or CD47. CD47-SIRPα interactions have been implicated in a number of cellular functions, including the regulation of neutrophil migration, memory formation, macrophage multinucleation, B cell aggregation, T cell activation, dendritic cell maturation and function, and red blood cell self-recognition in mice, (Kharitonenkov, et al., *Nature*, 386: 181, 1997; Han, et al., *J. Biol. Chem.*, 275: 37984, 2000; Chang, et al., *Learning & Memory*, 6: 448, 1999; Oldenborg, et al., *Science*, 288: 2051, 2000; Tanaka, et al., *Journal of Immunology*, 167(5): 2547-54, 2001; Liu, et al., v 277(12): 10028-36, 2002; Avice, et. al., *Journal of Immunology*, 167(5): 2459-68, 2001; Blazar, et al., *Journal of Experimental Medicine*, 194(4):541-9, 2001; Seiffert, et al., *Blood*, 97(9): 2741-9, 2001; Oldenborg, et al., *Journal of Experimental Medicine*, 193(7): 855-62, 2001; Pettersen, *Apoptosis*, 5(4): 299-306, 2000; Han, et al., *J. Biol. Chem.*, 275(48): 37984-92, 2000; Demeure, et al., *Journal of Immunology*, 164(4): 2193-9, 2000; Armant, et al., *Journal of Experimental Medicine*, 190(8): 1175-82, 1999; Jiang, et al., *J. Biol. Chem.*, 274(2): 559-62, 1999; Lee, et al., *European Journal of Neuroscience*, 12(3): 1105-12, 2000; and Chang, et al., *Learning & Memory*, 6(5): 448-57, 1999) although the mechanisms remain undefined.

Thus, a heretofore unaddressed need exists in the industry to modulate the interaction between CD47 and SIRPα.

SUMMARY OF THE INVENTION

Briefly described, embodiments of the present invention include polypeptides and polynucleotides. Representative polynucleotides include a polynucleotide selected from: the nucleotide sequence set forth in SEQ ID NO:1, or a degenerate variant of the SEQ ID NO:1; the nucleotide sequence set forth in SEQ ID NO:3, or a degenerate variant of the SEQ ID NO:3; the nucleotide sequence set forth in SEQ ID NO:5, or a degenerate variant of the SEQ ID NO:5; and the nucleotide sequence set forth in SEQ ID NO:7, or a degenerate variant of the SEQ ID NO:7.

In addition, the polynucleotides can include polynucleotides that encode an amino acid selected from: an amino acid sequence set forth in SEQ ID NO:2, or SEQ ID NO:2 with conservative amino acid substitutions; an amino acid sequence set forth in SEQ ID NO:4, or SEQ ID NO:4 with conservative amino acid substitutions; an amino acid sequence set forth in SEQ ID NO:6, or SEQ ID NO:6 with conservative amino acid substitutions; and an amino acid sequence set forth in SEQ ID NO:8, or SEQ ID NO:8 with conservative amino acid substitutions.

Representative polypeptides include an amino acid selected from: an amino acid sequence set forth in SEQ ID NO:2, or conservatively modified variants thereof; an amino acid sequence set forth in SEQ ID NO:4, or conservatively modified variants thereof; an amino acid sequence set forth in SEQ ID NO:6, or conservatively modified variants thereof; and an amino acid sequence set forth in SEQ ID NO:8, or conservatively modified variants thereof.

In addition, the polypeptides include an amino acid selected from: an amino acid sequence at least 50% identical to SEQ ID NO:2; an amino acid sequence at least 50% identical to SEQ ID NO:4; an amino acid sequence at least 50% identical to SEQ ID NO:6; or an amino acid sequence at least 50% identical to SEQ ID NO:8.

Further, embodiments of the present invention include representative methods of treating a condition by administering to a host in need of treatment an effective amount of a polypeptide. The polypeptides include an amino acid selected from: an amino acid sequence set forth in SEQ ID NO:2, or conservatively modified variants thereof; an amino acid sequence set forth in SEQ ID NO:4, or conservatively modified variants thereof; an amino acid sequence set forth in SEQ ID NO:6, or conservatively modified variants thereof; and an amino acid sequence set forth in SEQ ID NO:8, or conservatively modified variants thereof.

Furthermore, embodiments of the present invention include pharmaceutical compositions. A representative pharmaceutical composition includes a polypeptide in combination with a pharmaceutically acceptable carrier. The polypeptide includes an amino acid selected from: an amino acid sequence set forth in SEQ ID NO:2, or conservatively modified variants thereof; an amino acid sequence set forth in SEQ ID NO:4, or conservatively modified variants thereof; an amino acid sequence set forth in SEQ ID NO:6, or conservatively modified variants thereof; and an amino acid sequence set forth in SEQ ID NO:8, or conservatively modified variants thereof.

Still further, the polynucleotides can include polynucleotides that encode an amino acid selected from: an amino acid sequence set forth in SEQ ID NO:46, or SEQ ID NO:46 with conservative amino acid substitutions; an amino acid sequence set forth in SEQ ID NO:47, or SEQ ID NO:47 with conservative amino acid substitutions; an amino acid sequence set forth in SEQ ID NO:48, or SEQ ID NO:48 with conservative amino acid substitutions; and an amino acid sequence set forth in SEQ ID NO:49, or SEQ ID NO:49 with conservative amino acid substitutions.

Still further, representative polypeptides include an amino acid selected from: an amino acid sequence set forth in SEQ ID NO:46, or conservatively modified variants thereof; an amino acid sequence set forth in SEQ ID NO:47, or conservatively modified variants thereof; an amino acid sequence set forth in SEQ ID NO:48, or conservatively modified variants thereof; and an amino acid sequence set forth in SEQ ID NO:49, or conservatively modified variants thereof.

Still further, embodiments of the present invention include representative methods of treating a condition by administering to a host in need of treatment an effective amount of a polypeptide. The polypeptides include an amino acid selected from: an amino acid sequence set forth in SEQ ID NO:46, or conservatively modified variants thereof; an amino acid sequence set forth in SEQ ID NO:47, or conservatively modified variants thereof; an amino acid sequence set forth in SEQ ID NO:48, or conservatively modified variants thereof; and an amino acid sequence set forth in SEQ ID NO:49, or conservatively modified variants thereof.

Still further, embodiments of the present invention include pharmaceutical compositions. A representative pharmaceutical composition includes a polypeptide in combination with a pharmaceutically acceptable carrier. The polypeptide includes an amino acid selected from: an amino acid sequence set forth in SEQ ID NO:46, or conservatively modified variants thereof; an amino acid sequence set forth in SEQ ID NO:47, or conservatively modified variants thereof; an amino acid sequence set forth in SEQ ID NO:48, or conservatively modified variants thereof; and an amino acid sequence set forth in SEQ ID NO:49, or conservatively modified variants thereof.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 1 illustrates SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:46, SEQ ID NO:47, SEQ ID NO:48, and SEQ ID NO:49.

FIG. 4A illustrates specific peptide-bearing phage selected from panning with CL10 library, while FIG. 4B illustrates phage selected from panning with CL6 and LL9 libraries. Each phage was individually propagated, isolated and tested for specificity of binding to mAb C5/D5 by ELISA as described in experimental procedures below. The data represent the mean and the standard deviation of triplicate wells.

FIGS. 6A-6C are graphs that illustrate the effects of synthetic peptides on CD47-SIRPα binding. FIG. 6A illustrates the effect of peptide C5/D5.1 on CD47-SIRPα binding. Microtiter plates were coated with SIRPα1 extracellular domain fusion protein (SIRPα1-GST, 1 µg/ml) for 2 hr. After blocking, CD47-AP was added in the absence or presence of synthetic peptides C5/D5.1 and control peptides C5/D5.4, C5/D5.11 and C5/D5.12 (used as 1 mM each). "*" $p<0.01$. CD47-AP binding was then detected by assay of alkaline phosphatase activity and normalized with respect to binding in the absence of any peptide (CD47-AP only). FIG. 6B illustrates the effect of dose-dependent inhibition of CD47-SIRPα1 binding by peptide C5/D5.1 performed as in FIG. 6A but with increasing concentrations of peptide as indicated. FIG. 6C demonstrates that peptide C5/D5.1 directly binds to SIRα1-GST. Microtiter plates were coated with peptide C5/D5.1 (2 mM) or BSA. After blocking, coated wells were incubated with either SIRPα1-GST or CD47-AP. Binding of these proteins were detected by a goat anti-GST antibody followed by peroxidase conjugated anti-goat secondary (for detecting SIRPα1-GST) or directly developed for alkaline phosphatase activity (for detecting CD47-AP). All the data represent the mean and standard deviation of triplicate wells.

FIGS. 7A-7C are graphs that illustrate the effects of synthetic peptides on PMN transmigration. PMN migration across collagen-coated transwells was assayed as described in experimental procedure below. FIG. 7A illustrates PMN migration (2 hr duration) in the absence of peptide as compared to migration in the presence of 0.5 mM peptide C5/D5.1, control peptides C5D5.4, C5/D5.11, and C5/D5.12 (0.5 mM each). FIG. 7B illustrates that peptide C5/D5.1 dose-dependently inhibits PMN transmigration (1 hr migration) compared to the control peptide C5D5.4 as shown in FIG. 7C. Data represents mean standard deviation of three transwells per condition in one of three experiments.

DETAILED DESCRIPTION

Figure 2A:
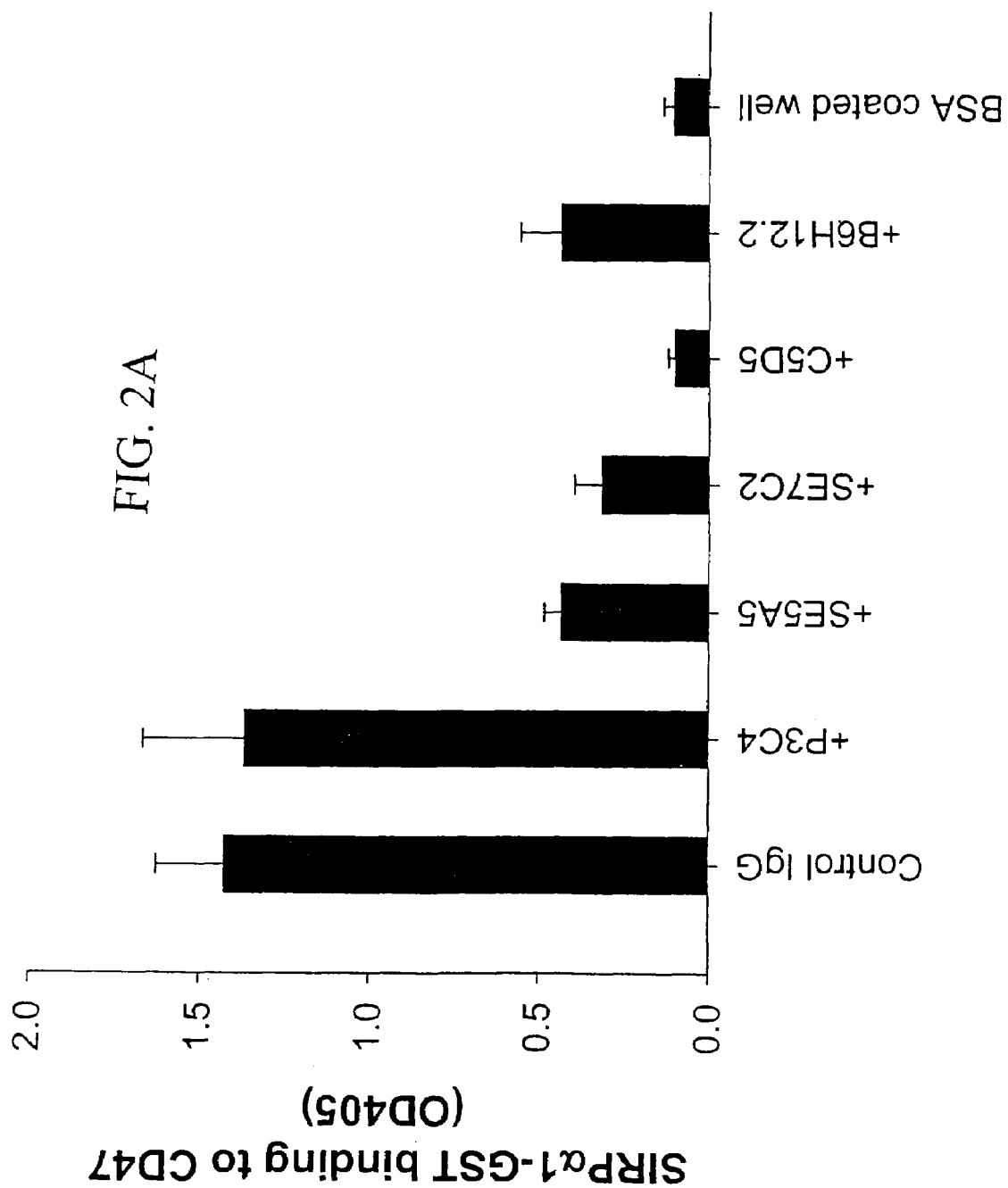
FIG. 2A is a bar graph (ELISA) that illustrates the marked inhibitory effects of SIRPα and CD47 mAbs on SIRPα-GST binding to purified CD47. Microtiter plates were coated with purified CD47 followed by blocking with BSA. Recombinant SIRPα1-GST was added at 10 micorgram per milliliter (µg/ml) in the presence or absence of 20 µg/ml anti SIRP mabs (P3C4, SE5A5, SE7C2) or anti CD47 mAbs (C5/D5, B6H12.2) followed by washing. Bound SIRP-GST was detected by ELISA after incubation with peroxidase conjugated goat anti GST and development with substrate.

Embodiments of the present invention provide for polypeptides that can be used to modulate SIRPα-CD47 functions. In addition, embodiments of the present invention also provide for polynucleotides that encode the polypeptides referred to above. Further, embodiments of the present invention provide for pharmaceutical compositions to treat conditions and methods of use thereof.

Prior to setting forth embodiments of the invention in detail, it may be helpful to first define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson, et al., *EMBO J*, 4:1075, 1985; Nilsson, et al., *Methods Enzymol.*, 198:3, 1991), glutathione S transferase (Smith, et al., *Gene*, 67:31, 1988), Glu-Glu affinity tag, substance P, Flag™ peptide (Hopp, et al., *Biotechnology*, 6:1204-10, 1988), streptavidin binding peptide, or other antigenic epitope or binding domain. See, in general, Ford, et al., *Protein Expression and Purification*, 2: 95-107, 1991. DNAs encoding affinity tags are available from commercial suppliers (e.g., Pharmacia Biotech, Piscataway, N.J.).

"Polynucleotide" generally refers to any polyribonucleotide or polydeoxyribonucleotide, which may be unmodified ribonucleic acid (RNA) or deoxyribonucleic acid (DNA) or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or INAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically, or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, (i.e., peptide isosteres). "Polypeptide" refers to both short chains, commonly referred to as peptides, oligopeptides, or oligomers, and to longer chains, generally referred to as proteins. "Polypeptides" may contain amino acids other than the 20 gene-encoded amino acids. "Polypeptides" include amino acid sequences modified either by natural processes, such as post-translational processing, or by chemical modification techniques, which are well known in the art. Such modifications are described in basic texts and in more detailed monographs, as well as in a voluminous research literature.

Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched, and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (Proteins—Structure and Molecular Properties, 2nd Ed., T. E. Creighton, W. H. Freeman and Company, New York, 1993; Wold, F., Post-translational Protein Modifications: Perspectives and Prospects, pgs. 1-12 in Post-translational Covalent Modification of Proteins, B. C. Johnson, Ed., Academic Press, New York, 1983; Seifter, et al., *Meth Enzymol*, 182: 626-646, 1990, and Rattan, et al., *Ann NY Acad. Sci.*, 663:48-62, 1992).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions, and truncations in the polypeptide encoded by the reference sequence, as discussed below.

A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including, but not limited to, those described in (*Computational Molecular Biology*, Lesk, A. M., Ed., Oxford University Press, New York, 1988; *Biocomputing: Informatics and Genome Projects*, Smith, D. W., Ed., Academic Press, New York, 1993; *Computer Analysis of Sequence Data, Part I*, Griffin, A. M., and Griffin, H. G., Eds., Humana Press, New Jersey, 1994; *Sequence Analysis in Molecular Biology*, von Heinje, G., Academic Press, 1987; and *Sequence Analysis Primer*, Gribskov, M. and Devereux, J., Eds., M Stockton Press, New York, 1991; and Carillo, H., and Lipman, D., *SIAM J Applied Math.*, 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (*J. Mol. Biol.*, 48: 443-453, 1970) algorithm (e.g., NBLAST, and XBLAST). The default parameters are used to determine the identity for the polynucleotides and polypeptides of the present invention.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

The term "expression vector" is used to denote a DNA molecule, linear or circular, which includes a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated polynucleotide molecules of the present invention are free of other polynucleotides with which they are ordinarily associated, but may include naturally occurring 5' and 3' untranslated regions such as promoters and terminators. The identification of associated regions will be evident to one of ordinary skill in the art (Dynan, et al., *Nature*, 316: 774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes (e.g., transcription initiates in the promoter and proceeds through the coding segment to the terminator).

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "condition" and "conditions" denote a state of health that can be related to processes involving the interaction of SIRPα and CD47. The processes that involve the interaction of SIRPα and CD47 are discussed below, and are to be included as condition(s) that can be treated by embodiments of the present invention.

The term "host" includes both humans, mammals (e.g., cats, dogs, horses, etc.), and other living species that are in need of treatment. Hosts that are "predisposed to" condition(s) can be defined as hosts that do not exhibit overt symptoms of one or more of these conditions but that are genetically, physiologically, or otherwise at risk of developing one or more of these conditions.

The term "treat", "treating", and "treatment" are an approach for obtaining beneficial or desired clinical results. For purposes of embodiments of this invention, beneficial or desired clinical results include, but are not limited to, alleviation of symptoms, diminishment of extent of disease, stabilization (i.e., not worsening) of disease, preventing spread (i.e., metastasis) of disease, delaying or slowing of disease progression, amelioration or palliation of the disease state, and remission (partial or total) whether detectable or undetectable. In addition, "treat", "treating", and "treatment" can also mean prolonging survival as compared to expected survival if not receiving treatment.

The term "modulate" and "modulation" denote adjustment or regulation of the activity of a compound or the interaction between one or more compounds.

All publications, including but not limited to patents and patent applications, cited in this specification are herein incorporated by reference as if each individual publication were specifically and individually indicated to be incorporated by reference herein as though fully set forth.

Discussion

As indicated above, a variety of conditions (e.g., inflammatory diseases, pulmonary diseases, urinary system diseases, central nervous system diseases, and gastrointestinal tract diseases) are characterized by migration of PMN through tissues and across mucosal surfaces. As discussed below, CD47 and SIRPα are important proteins in PMN functions as well as other functions. It should be noted that SIRPα and SIRPα1 are used interchangeably throughout this document.

In this regard, SIRPα directly and specifically binds to CD47, and therefore, is a cellular ligand for CD47 (Liu, et al., *J. Biol. Chem.*, 277: 10026). In addition, it has been shown that SIRPα-CD47 interactions serve to attenuate neutrophil migration in response to chemotactic stimuli by regulation of the rate of leukocyte migration (chemotaxis). Furthermore, others have shown that CD47 and/or SIRPα ligation in immune cells downregulates immune cell responses.

In particular, published reports strongly implicate SIRPα-CD47 binding interactions as playing an important role in: 1) down regulation of IL-12 responsiveness of T cells, 2) inhibition of phenotypic and functional maturation of immature Dendritic cells (DC), and 3) inhibition of cytokine production by mature DC. Thus, mimicry of these binding interactions would likely inhibit development of a TH1-type immune response.

In addition, SIRPα-CD47 interactions have been shown to be important in macrophage multinucleation in response to certain viral and bacterial pathogens. Thus, protocols devised at inhibition in macrophage multinucleation might by successfully employed to downregulate inappropriate inflammatory responses to pathogens. Further, inhibition of such responses might be important in devising therapies for inflammatory diseases such as, but not limited to, autoimmune disease and inflammatory bowel disease.

Others have shown that CD47 ligation with antibody (C5/D5) and/or SIRPα can result in T Cell anergy and inhibition of DC mediated induction of cytotxic T cell responses. Dysregulation of these immune responses under a number of conditions can give rise to pathophysiologic conditions that have grave consequences. In particular, agents that produce the same effect(s) as CD47 ligation may be useful in treatments aimed at inhibiting undesirable effects of graft versus host disease and other autoimmune syndromes resulting from excess or inappropriate T cell activation.

Furthermore, SIRPα-CD47 ligation results in diminished clearance of red blood cells (RBC) in conditions such as autoimmune hemolytic anemia, while decreased levels of CD47 results in enhanced clearance of RBC. Thus, agents that recapitulate CD47 function may inhibit inappropriate RBC destruction in autoimmune hemolytic anemia or related diseases.

Lastly, SIRPα-CD47 coupling in the central nervous system has been shown to be important in memory consolidation in rodents, while CD47 deficiency results in impaired short term memory formation. Consequently, agents that modulate CD47 function may promote CD47-SIRPα signaling interactions and hence improve memory.

Polypeptides of the present invention can modulate SIRPα-CD47 function by binding to the SIRPα protein surface, thereby regulating neutrophil (PMN) migration. In this regard, polypeptides of the present invention can compete with a specific inhibitory CD47 antibody (monoclonal antibody C5/D5) in binding functionally to purified CD47. In addition, polypeptides of the present invention can inhibit binding of CD47 to SIRPα, the cellular ligand of CD47. Further, polypeptides of the present invention can bind directly to SIRPα. As a result, polypeptides of the present invention can at least inhibit neutrophil migration towards chemotactic stimuli.

Thus, polypeptides of the present invention can modulate SIRPα-CD47 by mimicking the SIRPα-CD47 binding site. In this regard, polypeptides of the present invention may regulate neutrophil migration and be used to treat conditions related to inflammatory, pulmonary, urinary system, central nervous system, immune, and gastrointestinal tract diseases, for example. In particular, polypeptides of the present invention may be used as a treatment to inhibit development of a TH1-type immune response, inhibit undesirable effects of graft versus host disease and autoimmune syndromes, inhibit inappropriate RBC destruction in autoimmune hemolytic anemia or related diseases, and improve memory.

Polypeptides and Polynucleotides

As indicated above, embodiments of the present invention include polypeptides and polynucleotides that encode the polypeptides. Embodiments of the polypeptide are designated "CERVIG polypeptides", while embodiments of the polynucleotides are designated "CERVIG polynucleotides." The CERVIG nucleotide sequences are set forth in SEQ ID NO:1, SEQ ID NO:3, SEQ ID NO:5, and SEQ ID NO:7, and the corresponding CERVIG polypepetide amino acid sequences are set forth in SEQ ID NO:2, SEQ ID NO:4, SEQ ID NO:6, and SEQ ID NO:8 (i.e., SEQ ID NO:1 corresponds to SEQ ID NO:2, SEQ ID NO:3 corresponds to SEQ ID NO:4, and so on). In addition, CERVIG polypeptides include SEQ ID NO:46, SEQ ID NO:47, SEQ ID NO:48, and SEQ ID NO:49.

CERVIG polynucleotide set forth in SEQ ID NO:1 has 36 nucleotides and has an approximate weight of 12 kilodaltons (kD). CERVIG polynucleotide set forth in SEQ ID NO:3 has 36 nucleotides and has an approximate weight of 12 kD. CERVIG polynucleotide set forth in SEQ ID NO:5 has 36 nucleotides and has an approximate weight of 12 kD. CERVIG polynucleotide set forth in SEQ ID NO:7 has 36 nucleotides and has an approximate weight of 12 kD.

CERVIG polypeptide set forth in SEQ ID NO:2 is a 12 amino acid polypeptide having an approximate weight of 1.3 kD. CERVIG polypeptide set forth in SEQ ID NO:4 is a 12 amino acid polypeptide having an approximate weight of 1.3 kD. CERVIG polypeptide set forth in SEQ ID NO:6 is a 12 amino acid polypeptide having an approximate weight of 1.3 kD. CERVIG polypeptide set forth in SEQ ID NO:8 is a 12 amino acid polypeptide having an approximate weight of 1.3 kD.

The CERVIG polynucleotides SEQ ID NO:1, SEQ ID NO:3, SEQ ID NO:5, and SEQ ID NO:7 encode the CERVIG polypeptides SEQ ID NO:2, SEQ ID NO:4, SEQ ID NO:6, and SEQ ID NO:8, respectively.

CERVIG polypeptides set forth in SEQ ID NO:2, SEQ ID NO:4, SEQ ID NO:6, SEQ ID NO:8, SEQ ID NO:46, SEQ ID NO:47, SEQ ID NO:48, and SEQ ID NO:49 are not represented in the linear sequence of either CD47 (SEQ ID NO: 9) or SIRPα, which indicates that CERVIG polypeptides represent a tertiary structure on the surface of CD47 and SIRPα.

As discussed above, embodiments of the present invention provide CERVIG polynucleotides, including DNA and RNA molecules, that encode the CERVIG polypeptides. Those skilled in the art will readily recognize that, in view of the degeneracy of the genetic code, considerable sequence variation is possible among these polynucleotide molecules. SEQ ID NO:1, SEQ ID NO:3, SEQ ID NO:5, and SEQ ID NO:7 are degenerate polynucleotide sequences that encompasses polynucleotides that encode CERVIG polypeptides of SEQ ID NO:2, SEQ ID NO:4, SEQ ID NO:6, and SEQ ID NO:8, respectively. Table 1 sets forth the one-letter codes that maybe used within SEQ ID NO:1, SEQ ID NO:3, SEQ ID NO:5, and SEQ ID NO:7 to denote degenerate nucleotide positions. "Resolutions" are the nucleotides denoted by a code letter. "Nucleotide Complement" indicates the code for the complementary nucleotide(s). For example, the code Y denotes either C (cytosine) or T, and its complement R denotes A (adenosine) or G (guanine), A being complementary to T, and G being complementary to C.

TABLE 1

| BASE CODE | RESOLUTIONS | BASE CODE | NUCLEOTIDE |
|---|---|---|---|
| A | A | T | T |
| C | C | G | G |
| G | G | C | C |
| T | T | A | A |
| R | A-G | Y | C-T |
| Y | C-T | R | A-G |
| M | A-C | K | G-T |
| K | G-T | M | A-C |
| S | C-G | S | C-G |
| W | A-T | W | A-T |
| H | A-C-T | D | A-G-T |
| B | C-G-T | V | A-C-G |
| V | A-C-G | B | C-G-T |
| D | A-G-T | H | A-C-T |
| N | A-C-G-T | N | A-C-G-T |

The degenerate codons used in SEQ ID NO:1 SEQ ID NO:3, SEQ ID NO:5, and SEQ ID NO:7, encompassing possible codons for a given amino acid, are set forth in Table 2.

TABLE 2

| THREE LETTER CODE | ONE LETTER CODE | SYNONYMOUS CODONS | DEGENERATE CODON |
|---|---|---|---|
| Cys | C | TGC TGT | TGY |
| Ser | S | AGC AGT TCA TCC TCG TCT | WSN |
| Thr | T | ACA ACC ACG ACT | CAN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |

TABLE 2-continued

| THREE LETTER CODE | ONE LETTER CODE | SYNONYMOUS CODONS | DEGENERATE CODON |
|---|---|---|---|
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Asn-Asp | B | | RAY |
| Glu-Gln | Z | | SAR |
| Any | X | | NNN |

One of ordinary skill in the art will appreciate that some ambiguity is introduced in determining a degenerate codon. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2 SEQ ID NO:4, SEQ ID NO:6, and SEQ ID NO:8.

One of ordinary skill in the art would be able to generate polynucleotides sequences for SEQ ID NO:46, SEQ ID NO:47, SEQ ID NO:48, and SEQ ID NO:49, from Tables 1 and 2.

Variant CERVIG polynucleotides that encode polypeptides that can treat a condition as defined above are within the scope of the embodiments of the present invention. More specifically, variant CERVIG polynucleotides that encode polypeptides which exhibit at least about 58%, about 66%, about 75%, about 83%, and preferably about 92%, of the activity of CERVIG polypeptides encoded by the variant CERVIG polynucleotide are within the scope of the embodiments of the present invention.

For any CERVIG polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise CERVIG variants (i.e., polynucleotides and polypeptides) based upon the polynucleotide and amino acid sequences described herein.

As indicated above, CERVIG polynucleotides and isolated CERVIG polynucleotides of the present invention can include DNA and RNA molecules. Methods for preparing DNA and RNA are well known in the art. In general, RNA is isolated from a tissue or cell that produces CERVIG RNA. Such tissues and cells can be identified by Northern blotting (Thomas, Proc. Natl. Acad. Sci. USA, 77: 5201, 1980). An exemplary source being human testis tissue. Total RNA can be prepared using guanidine HCl extraction followed by isolation by centrifugation in a CsCl gradient (Chirgwin, et al., *Biochemistry*, 18:,52-94, 1979). Complementary DNA (cDNA) can be prepared from the RNA using known methods. In the alternative, genomic DNA can be isolated. Polynucleotides encoding CERVIG polypeptides are then identified and isolated by hybridization or PCR, for example.

CERVIG polynucleotides can also be synthesized using techniques widely known in the art. (Glick, et al., *Molecular Biotechnology, Principles & Applications of Recombinant*

DNA, (ASM Press, Washington, D.C. 1994); Itakura, et al., *Annu. Rev. Biochem.*, 53: 323-56, 1984 and Climie, et al., *Proc. Natl. Acad. Sci. USA,* 87: 633-7, 1990.

Embodiments of the present invention also provide for CERVIG polypeptides and isolated CERVIG polypeptides that are substantially homologous to the CERVIG polypeptides of SEQ ID NO:2, SEQ ID NO:4, SEQ ID NO:6, SEQ ID NO:8, SEQ ID NO:46, SEQ ID NO:47, SEQ ID NO:48, and SEQ ID NO:49. The term "substantially homologous" is used herein to denote polypeptides having about 50%, about 58%, about 65%, about 75%, about 83%, and preferably about 92% sequence identity to the sequences shown in SEQ ID NO:2, SEQ ID NO:4, SEQ ID NO:6, SEQ ID NO:8, SEQ ID NO:46, SEQ ID NO:47, SEQ ID NO:48, and SEQ ID NO:49. Percent sequence identity is determined by conventional methods as discussed above. In addition, embodiments of the present invention include polynucleotides that encode homologous polypeptides.

In general, homologous polypeptides are characterized as having one or more amino acid substitutions, deletions, and/or additions. These changes are preferably of a minor nature, that is conservative amino acid substitutions and other substitutions that do not significantly affect the activity of the polypeptide; small substitutions, typically of one to about six amino acids; and small amino- or carboxyl-terminal extensions, such as an amino-terminal methionine residue, a small linker peptide of up to about 2-6 residues, or an affinity tag. Homologous polypeptides comprising affinity tags can further comprise a proteolytic cleavage site between the homologous polypeptide and the affinity tag.

In addition, embodiments of the present invention include polynucleotides that encode polypeptides having one or more "conservative amino acid substitutions," compared with the CERVIG polypeptide of SEQ ID NO:2, SEQ ID NO:4, SEQ ID NO:6, SEQ ID NO:8, SEQ ID NO:46, SEQ ID NO:47, SEQ ID NO:48, or SEQ ID NO:49. Conservative amino acid substitutions can be based upon the chemical properties of the amino acids. That is, variants can be obtained that contain one or more amino acid substitutions of SEQ ID NO:2, SEQ ID NO:4, SEQ ID NO:6, SEQ ID NO:8, SEQ ID NO:46, SEQ ID NO:47, SEQ ID NO:48, or SEQ ID NO:49, in which an alkyl amino acid is substituted for an alkyl amino acid in a CERVIG polypeptide, an aromatic amino acid is substituted for an aromatic amino acid in a CERVIG polypeptide, a sulfur-containing amino acid is substituted for a sulfur-containing amino acid in a CERVIG polypeptide, a hydroxy-containing amino acid is substituted for a hydroxy-containing amino acid in a CERVIG polypeptide, an acidic amino acid is substituted for an acidic amino acid in a CERVIG polypeptide, a basic amino acid is substituted for a basic amino acid in a CERVIG polypeptide, or a dibasic monocarboxylic amino acid is substituted for a dibasic monocarboxylic amino acid in a CERVIG polypeptide.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. Other conservative amino acid substitutions are provided in Table 3.

TABLE 3

| CHARACTETISTIC | AMINO ACID |
| --- | --- |
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Conservative amino acid changes in CERVIG polypeptides can be introduced by substituting nucleotides for the nucleotides recited in SEQ ID NO:1, SEQ ID NO:3, SEQ ID NO:5, and SEQ ID NO:7. Such "conservative amino acid" variants can be obtained, for example, by oligonucleotide-directed mutagenesis, linker-scanning mutagenesis, mutagenesis using the polymerase chain reaction, and the like (McPherson (Ed.), *Directed Mutagenesis: A Practical Approach* (IRL Press 1991)). The ability of such variants to treat conditions as well as other properties of the wild-type protein can be determined using a standard methods. Alternatively, variant CERVIG polypeptides can be identified by the ability to specifically bind anti-CERVIG antibodies.

CERVIG polypeptides having conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., *J. Am. Chem. Soc.,* 113: 2722, 1991; Ellman, et al., *Methods Enzymol.,* 202: 301, 1991; Chung, et al., *Science,* 259: 806-9, 1993; and Chung, et al., *Proc. Natl. Acad. Sci. USA,* 90: 10145-9, 1993). In a second method, translation is carried out in *Xenopus oocytes* by microinjection of mutated mRNA and chemically aminoacylated suppressor tRNAs (Turcatti, et al., *J. Biol. Chem.,* 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., *Biochem.*, 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., *Protein Sci.*, 2: 395-403, 1993).

A limited number (i.e., less than 6) of non-conservative amino acids, amino acids that are not encoded by the genetic code, non-naturally occurring amino acids, and unnatural amino acids may be substituted for CERVIG polypeptide amino acid residues.

Essential amino acids in the polypeptides of the present invention can be identified according to procedures known in the art, such as site-directed mutagenesis or alanine-scanning mutagenesis (Cunningham, et al., *Science*, 244: 1081-5, 1989; Bass, et al., *Proc. Natl. Acad. Sci. USA*, 88: 4498-502, 1991). In the latter technique, single alanine mutations are introduced at every residue in the molecule, and the resultant mutant molecules are tested for biological activity as disclosed below to identify amino acid residues that are critical to the activity of the molecule. (Hilton, et al., *J. Biol. Chem.*, 271: 4699-708, 1996). Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. (de Vos, et al., *Science*, 255: 306-12, 1992; Smith, et al., *J. Mol. Biol.*, 224: 899-904, 1992; Wlodaver, et al., *FEBS Lett.*, 309: 59-64, 1992). The identities of essential amino acids can also be inferred from analysis of homologies with related nuclear membrane bound proteins.

Multiple amino acid substitutions can be made and tested using known methods of mutagenesis and screening, such as those disclosed by Reidhaar-Olson and Sauer (*Science*, 241: 53-7, 1988) or Bowie and Sauer (*Proc. Natl. Acad. Sci. USA*, 86: 2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (Lowman, et al., *Biochem.*, 30: 10832-7, 1991; Ladner, et al., U.S. Pat. No. 5,223,409) and region-directed mutagenesis (Derbyshire, et al., *Gene*, 46:145, 1986; Ner, et al., *DNA*, 7:127, 1988).

Variants of the disclosed CERVIG polypeptides can be generated through DNA shuffling. (Stemmer, *Nature*, 370: 389-91, 1994 and Stemmer, *Proc. Natl. Acad. Sci. USA*, 91: 10747-51, 1994). Briefly, variant polypeptides are generated by in vitro. homologous recombination by random fragmentation of a parent DNA followed by reassembly using PCR, resulting in randomly introduced point mutations. This technique can be modified by using a family of parent DNAs, such as allelic variants or genes from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods can be combined with high-throughput, automated screening methods to detect activity of cloned, mutagenized polypeptides in host cells. Preferred assays in this regard include cell proliferation assays and biosensor-based ligand-binding assays. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of CERVIG polypeptide fragments or variants of SEQ ID NO:2, SEQ ID NO:4, SEQ ID NO:6, SEQ ID NO:8, SEQ ID NO:46, SEQ ID NO:47, SEQ ID NO:48, and SEQ ID NO:49 that retain the functional properties of the CERVIG polypeptide. Such polypeptides may also include additional polypeptide segments as generally disclosed herein.

For any CERVIG polypeptide, including variants and fusion proteins, one of ordinary skill in the art can readily generate a degenerate polynucleotide sequence encoding that variant using the information set forth in Tables 1 and 2 above.

As used herein, a fusion protein consists essentially of a first portion and a second portion joined by a peptide bond. In one embodiment the first portion includes a polypeptide comprising a sequence of amino acid residues that is at least about 50%, about 57, about 65%, about 75%, about 83%, and preferably about 92% identical in amino acid sequence to SEQ ID NO:2, SEQ ID NO:4, SEQ ID NO:6, SEQ ID NO:8, SEQ ID NO:46, SEQ ID NO:47, SEQ ID NO:48, or SEQ ID NO:49 and the second portion is any other heterologous non CERVIG polypeptide. The other polypeptide may be polypeptides that do not inhibit the function of the CERVIG polypeptide, such as a signal peptide to facilitate secretion of the fusion protein or an affinity tag.

The CERVIG polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells. (Sambrook et al., *Molecular Cloning: A Laboratory Manual*, 2nd Ed., Cold Spring Harbor Laboratory Press, Cold Spring Harbor, N.Y., 1989, and Ausubel, et al., Eds., *Current Protocols in Molecular Biology*, John Wiley and Sons, Inc., N.Y., 1987).

In general, CERVIG polynucleotides sequence encoding CERVIG polypeptides are operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a CERVIG polypeptide into the secretory pathway of a host cell, a secretory signal sequence (also known as a leader sequence, signal sequence, prepro sequence or pre sequence) is provided in the expression vector. The secretory signal sequence may be derived from another secreted protein or synthesized de novo. The secretory signal sequence is operably linked to the CERVIG polynucleotide sequence, (i.e., the two sequences are joined in the correct reading frame and positioned to direct the newly synthesized polypeptide into the secretory pathway of the host cell). Secretory signal sequences are commonly positioned 5' to the polynucleotide sequence encoding the polypeptide of interest, although certain secretory signal sequences may be positioned elsewhere in the polynucleotide sequence of interest (U.S. Pat. No. 5,037,743, U.S. Pat. No. 5,143,830).

It is preferred to purify the CERVIG polypeptides of the present invention to about 80% purity, more preferably to about 90% purity, even more preferably about 95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant CERVIG polypeptides (or fusion CERVIG polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. (Affinity Chromatography: Principles & Methods, Pharmacia LKB Biotechnology, Uppsala, Sweden, 1988).

The CERVIG polypeptides of the present invention can be isolated by exploitation of their binding properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, Trends in Biochem., 3: 1-7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (Methods in Enzymol., 182, M. Deutscher, (Ed.), Acad. Press, San Diego, 1990, pp. 529-39). Within additional embodiments of the invention, a fusion of the polypeptide of interest and an affinity tag (e.g., Glu-Glu tag) may be constructed to facilitate purification.

CERVIG polypeptides or fragments thereof may also be prepared through chemical synthesis according to methods known in the art, including exclusive solid phase synthesis, partial solid phase methods, fragment condensation or classical solution synthesis. (Merrifield, J. Am. Chem. Soc., 85: 2149, 1963).

Using methods known in the art, CERVIG polypeptides may be prepared as monomers or multimers; glycosylated or non-glycosylated; and pegylated or non-pegylated.

An in vivo approach for assaying CERVIG polypeptides involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (Becker, et al., Meth. Cell Biol., 43: 161-89, 1994; and Douglas, et al., Science & Medicine, 4: 44-53). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

The CERVIG polypeptide can be inserted into portions of the adenovirus by deleting a portion of the adenovirus genome. The CERVIG polypeptide may be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the CERVIG polypeptide or conjugates of the CERVIG polypeptide. Secreted proteins will enter the circulation in the highly vascularized liver, and effects on the condition to be treated can be determined.

CERVIG polypeptides can also be used to prepare antibodies that may bind to CD47 and/or inhibit CD47 function including SIRPα binding. The CERVIG polypeptide or a fragment thereof serves as an antigen (immunogen) to inoculate an animal and elicit an immune response. Suitable antigens would be the CERVIG polypeptide encoded by SEQ ID NO:2, for example. Antibodies generated from this immune response can be isolated and purified as described herein. Methods for preparing and isolating polyclonal and monoclonal antibodies are well known in the art. (Current Protocols in Immunology, Cooligan, et al. (Eds.), National Institutes of Health, John Wiley and Sons, Inc., 1995; Sambrook, et al., Molecular Cloning: A Laboratory Manual, Second Edition, Cold Spring Harbor, N.Y., 1989; and Hurrell, (Ed.), Monoclonal Hybridoma Antibodies: Techniques and Applications, CRC Press, Inc., Boca Raton, Fla., 1982

As would be evident to one of ordinary skill in the art, polyclonal antibodies can be generated from inoculating a variety of warm-blooded animals such as horses, cows, goats, sheep, dogs, chickens, rabbits, mice, and rats with a CERVIG polypeptide or a fragment thereof. The immunogenicity of a CERVIG polypeptide may be increased through the use of an adjuvant, such as alum (aluminum hydroxide) or Freund's complete or incomplete adjuvant. Polypeptides useful for immunization also include fusion polypeptides, such as fusions of CERVIG or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to CERVIG polypeptides, and selection of antibody display libraries in phage or similar vectors (for instance, through use of immobilized or labeled CERVIG polypeptide). Genes encoding polypeptides having potential CERVIG polypeptides binding domains can be obtained by screening random peptide libraries displayed on phage (phage display) or on bacteria, such as E. coli. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner, et al., U.S. Pat. No. 5,223,409; Ladner, et al., U.S. Pat. No. 4,946,778; Ladner, et al., U.S. Pat. No. 5,403,484 and Ladner, et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.).

Embodiments of the present invention also provide for isolated and purified CERVIG polynucleotide probes or primers. CERVIG polynucleotide probes can be RNA or DNA. DNA can be either cDNA or genomic DNA. In general, polynucleotide probes are single or double-stranded DNA or RNA, generally synthetic oligonucleotides, but may be generated from cloned cDNA or genomic sequences and will generally comprise at least 16 nucleotides, between about 17 and 25 nucleotides, and between about 25 and 36 nucleotides. Probes and primers are generally synthetic oligonucleotides, but may be generated from cloned cDNA or genomic sequences or its complements. Analytical probes will generally be about 20 nucleotides in length, although somewhat shorter probes (14-17 nucleotides) can be used. PCR primers are at least 5 nucleotides in length, preferably 15 or more nucleotides, more preferably 20-30 nucleotides.

Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art. Techniques for developing polynucleotide probes and hybridization techniques are known in the art. (Ausubel, et al., Eds., *Current Protocols in Molecular Biology*, John Wiley and Sons, Inc., N.Y., 1991).

CERVIG polypeptides may be used within diagnostic systems to detect the presence of CD47 binding partners such as SIRPα. The information derived from such detection methods would provide insight into the significance of CERVIG polypeptides in various diseases, and can serve as diagnostic tools for diseases for which altered levels of CD47 and/or SIRPα are significant. Altered levels of CERVIG polypeptides may be indicative of pathological conditions, as defined above.

In a basic assay, a single-stranded probe molecule is incubated with RNA, isolated from a biological sample, under conditions of temperature and ionic strength that promote base pairing between the probe and target CERVIG polynucleotide. After separating unbound probe from hybridized molecules, the amount of hybrids is detected.

Well-established hybridization methods of polypeptide detection include northern analysis and dot/slot blot hybridization (Ausubel, et al., Eds., *Current Protocols in Molecular Biology*, John Wiley and Sons, Inc., N.Y., 1991, and Wu, et al. (Eds.), "Analysis of Gene Expression at the RNA Level," in *Methods in Gene Biotechnology*, pages 225-239 (CRC Press, Inc. 1997)). Nucleic acid probes can be detectably labeled with radioisotopes such as $^{32}P$ or $^{35}S$. Alternatively, CERVIG polynucleotide can be detected with a nonradioactive hybridization method (Isaac (ed.), Protocols for Nucleic Acid Analysis by Nonradioactive Probes, Humana Press, Inc., 1993). Typically, nonradioactive detection is achieved by enzymatic conversion of chromogenic or chemiluminescent substrates. Illustrative nonradioactive moieties include biotin, fluorescein, and digoxigenin.

CERVIG polynucleotide probes are also useful for in vivo diagnosis. As an illustration, $^{18}F$-labeled CERVIG polynucleotides can be administered to a subject and visualized by positron emission tomography (Tavitian, et al., *Nature Medicine*, 4: 467, 1998).

Numerous diagnostic procedures take advantage of the polymerase chain reaction (PCR) to increase sensitivity of detection methods. Standard techniques for performing PCR are well-known (Mathew (Ed.), *Protocols in Human Molecular Genetics*, (Humana Press, Inc. 1991), White (Ed.), *PCR Protocols: Current Methods and Applications* (Humana Press, Inc. 1993), Cotter (Ed.), *Molecular Diagnosis of Cancer* (Humana Press, Inc. 1996), Hanausek and Walaszek (Eds.), *Tumor Marker Protocols*, (Humana Press, Inc. 1998), Lo (Ed.), *Clinical Applications of PCR* (Humana Press, Inc. 1998), and Meltzer (Ed.), *PCR in Bioanalysis*

(Humana Press, Inc. 1998)). PCR primers can be designed to amplify a sequence encoding a particular CD47 and/or SIRP region of homology.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled CERVIG polynucleotide probe, and examined by autoradiography. Additional alternative approaches include the use of digoxigenin-labeled deoxyribonucleic acid triphosphates to provide chemiluminescence detection, and the C-TRAK colorimetric assay.

Formulations

The CERVIG polypeptides and the pharmaceutically acceptable salts and solvates thereof can be prepared in a physiologically acceptable formulation, such as in a pharmaceutically acceptable carrier medium and/or excipient, using known techniques. For example, the CERVIG polypeptide can be combined with a pharmaceutically acceptable excipient to form a therapeutic composition (hereinafter CERVIG composition).

Alternatively, the CERVIG polynucleotide for the CERVIG polypeptide can delivered in a vector for continuous administration using gene therapy techniques. The vector may be administered in a vehicle having specificity for a target site, such as a tumor.

By "pharmaceutically acceptable salt" it is meant those salts which are, within the scope of sound medical judgement, suitable for use in contact with the tissues of hosts without undue toxicity, irritation, allergic response and the like, and are commensurate with a reasonable benefit/risk ratio and effective for their intended use.

CERVIG compositions may be suitable for oral, rectal, nasal, topical (including buccal and sublingual), vaginal, or parenteral (including subcutaneous, intramuscular, subcutaneous, intravenous, intradermal, intraocular, intratracheal, intracistemal, intraperitorneal, and epidural) administration.

CERVIG compositions may conveniently be presented in unit dosage form and may be prepared by conventional pharmaceutical techniques. Such techniques include the step of bringing into association a CERVIG polypeptide and one or more pharmaceutical carriers or excipients.

CERVIG compositions suitable for oral administration may be presented as discrete units such as, but not limited to, tablets, caplets, pills or dragees capsules, or cachets, each containing a predetermined amount of one or more of the compositions; as a powder or granules; as a solution or a suspension in an aqueous liquid or a non-aqueous liquid; or as an oil-in-water liquid emulsion or a water-in-oil emulsion or as a bolus, etc.

CERVIG compositions suitable for topical administration in the mouth include for example, lozenges, having the ingredients in a flavored basis, usually sucrose and acacia or tragacanth; pastilles, having a CERVIG polypeptide in an inert basis such as gelatin and glycerin, or sucrose and acacia; and mouthwashes, having one or more of the compositions of the present invention administered in a suitable liquid carrier.

CERVIG compositions suitable for topical administration to the skin may be presented as ointments, creams, gels, and pastes, having a CERVIG polypeptide administered in a pharmaceutical acceptable carrier.

CERVIG compositions for rectal administration may be presented as a suppository with a suitable base comprising, for example, cocoa butter or a salicylate.

CERVIG compositions suitable for nasal administration, when the carrier is a solid, include a coarse powder having a particle size, for example, in the range of 20 to 500 microns which is administered in the manner in which snuff is taken, (i.e., by rapid inhalation through the nasal passage from a container of the powder held close up to the nose). When the carrier is a liquid (for example, a nasal spray or as nasal drops), CERVIG polypeptides can be admixed in an aqueous or oily solution, and inhaled or sprayed into the nasal passage.

CERVIG compositions suitable for vaginal administration may be presented as pessaries, tampons, creams, gels, pastes, foams or spray formulations containing a CERVIG polypeptide and appropriate carriers.

CERVIG compositions suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. CERVIG compositions may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets of the kind previously described above.

Pharmaceutical organic or inorganic solid or liquid carrier media suitable for enteral or parenteral administration can be used to fabricate the compositions. Gelatin, lactose, starch, magnesium stearate, talc, vegetable and animal fats and oils, gum, polyalkylene glycol, water, or other known carriers may all be suitable as carrier media.

CERVIG compositions may be used as the active ingredient in combination with one or more pharmaceutically acceptable carrier mediums and/or excipients. As used herein, "pharmaceutically acceptable carrier medium" includes any and all carriers, solvents, diluents, or other liquid vehicles, dispersion or suspension aids, surface active agents, isotonic agents, thickening or emulsifying agents, preservatives, solid binders, lubricants, adjuvants, vehicles, delivery systems, disintegrants, absorbents, preservatives, surfactants, colorants, flavorants, or sweeteners and the like, as suited to the particular dosage form desired.

Additionally, CERVIG compositions may be combined with pharmaceutically acceptable excipients, and, optionally, sustained-release matrices, such as biodegradable polymers, to form therapeutic compositions. A "pharmaceutically acceptable excipient" refers to a non-toxic solid, semi-solid or liquid filler, diluent, encapsulating material or formulation auxiliary of any type.

Except insofar as any conventional carrier medium is incompatible with CERVIG compositions used in practicing embodiments of the invention, such as by producing any undesirable biological effect or otherwise interacting in a deleterious manner with CERVIG polypeptides of the pharmaceutical composition, its use is contemplated to be within the scope of the embodiments of this invention.

When used in the above or other treatments, a therapeutically effective amount of CERVIG compositions may be employed in pure form or, where such forms exist, in pharmaceutically acceptable salt. By a "therapeutically effective amount" of a CERVIG polypeptide it is meant a sufficient amount of one or more of the components to treat a condition, at a reasonable benefit/risk ratio applicable to any medical treatment.

It will be understood, however, that the total daily usage of CERVIG compositions will be decided by the attending physician within the scope of sound medical judgment. The specific therapeutically effective dose level for any particular host will depend upon a variety of factors, including for example, the disorder being treated and the severity of the disorder; activity of the specific composition employed; the specific composition employed, the age, body weight, general health, sex and diet of the patient; the time of administration; route of administration; rate of excretion of the specific compound employed; the duration of the treatment; drugs used in combination or coincidential with the specific composition employed; and like factors well known in the medical arts. For example, it is well within the skill of the art to start doses of CERVIG compositions at levels lower than those required to achieve the desired therapeutic effect and to gradually increase the dosage until the desired effect is achieved.

CERVIG compositions are preferably formulated in dosage unit form for ease of administration and uniformity of dosage. "Dosage unit form" as used herein refers to a physically discrete unit of CERVIG composition appropriate for the host to be treated. Each dosage should contain the quantity of CERVIG compositions calculated to produce the desired therapeutic affect either as such, or in association with the selected pharmaceutical carrier medium.

In general, the starting dose of most Phase I clinical trials is based on preclinical testing, and is usually quite conservative. A standard measure of toxicity of a drug in preclinical testing is the percentage of animals (rodents) that die because of treatment. The dose at which 10% of the animals die is known as the $LD_{10}$, which has in the past often correlated with the maximal-tolerated dose (MTD) in humans, adjusted for body surface area. The adjustment for body surface area includes host factors such as, for example, surface area, weight, metabolism, tissue distribution, absorption rate, and excretion rate. Thus, the standard conservative starting dose is one tenth the murine $LD_{10}$, although it may be even lower if other species (i.e., dogs) were more sensitive to the drug. It is anticipated that a starting dose for CERVIG compositions in Phase I clinical trials in humans will be determined in this manner. (Freireich E J, et al., *Cancer Chemother Rep* 50: 219-244, 1966).

As stated above, a therapeutically effective dose level will depend on many factors. In addition, it is well within the skill of the art to start doses of CERVIG compositions at relatively low levels, and increase the dosage until the desired effect is achieved.

CERVIG compositions may be used in combination with other CERVIG compositions, medicines and/or procedures for the treatment of the conditions described above.

CERVIG compositions may be used with a sustained-release matrix. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

As indicated above, CERVIG compositions may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The liposome can contain, in addition to CERVIG compositions, stabilizers, preservatives, excipients, and the like. The preferred lipids are the phospholipids and the phosphatidyl cholines (lecithins), both natural and synthetic. Methods to form liposomes are known in the art.

EXAMPLE 1

Antibodies against CD47 or SIRPα can inhibit CD47-SIRPα1 interactions. Within a panel of anti-CD47 antibodies, mAb C5/D5 were found to potently inhibit CD47-SIRPα1 interactions (Liu, et al., *J. Biol. Chem.*, 277(12): 10028-36, 2002). Thus, it is highly possible that C5/D5 epitope represents, in partial, the SIRPα binding site on CD47. To gain further understanding of the interactions between CD47 and SIRPα, phage display technology was used to pan the anti-CD47 monoclonal antibody C5/D5. By panning structural linear and constrained random-sequence peptide phage display libraries expressed in bacteriophage M13, C5/D5 binding sequence was identified, peptide C5/D5.1, CERVIGTGWVRC (SEQ ID NO:2). In addition to representing the epitope for mAb C5/D5 that competitively blocks CD47-C5/D5 binding, the synthetic peptide of this sequence can directly bind to SIRPα1 and thus competes with CD47-SIRPα1 binding. Furthermore, this peptide inhibits PMN transepithelial migration, which supports the idea that this sequence binds SIRPα on PMN similar as soluble CD47 (CD47-AP) and thus influences PMN function. Since C5/D5.1 is not presented as a linear sequence on CD47, this peptide is most likely represented in the tertiary structure of CD47 as a discontinuous group of amino acid residues on its surface and comprises a functional domain that interacts with SIRPα.

CD47 Binds Specifically to SIRPα and Binding is Inhibited by Anti-SIRP and Anti-CD47 Antibodies.

Results of SIRPα and CD47 mAbs on SIRPα-GST binding to purified CD47 is shown in FIG. 2A. MAbs were mixed with SIRPα-GST at 10 μg/ml in HBSS containing 0.5% BSA before adding to microtiter wells coated with CD47 purified from PMN. As can be seen, anti-SIRP mAbs SE5A5 and SE7C2 directly inhibited binding of SIRPα to purified CD47. In contrast, mAb P3C4 failed to inhibit this binding. These results are in good agreement with previous studies of CD47 expressing Jurkat cell adherence to SIRPα-GST (Seiffert, et al., *Blood*, 94: 3633) and demonstrate that anti-SIRPα1 mAbs (SE5A5, SE7C2 and SE12C3) inhibit cell adhesion by directly blocking CD47-SIRPα1 interactions. Anti-CD47 antibodies C5/D5 and B6H12.6 (10 μg/ml of each) were also tested. These mAbs have previously been shown to inhibit PMN transmigration (Liu, et al. *J. Biol. Chem.*, 276: 40156). As shown in FIG. 2A, these anti-CD47 mAbs also directly inhibited PMN CD47-SIRPα1 binding, with mAb C5/D5 being the most potent.

Figure 2B:
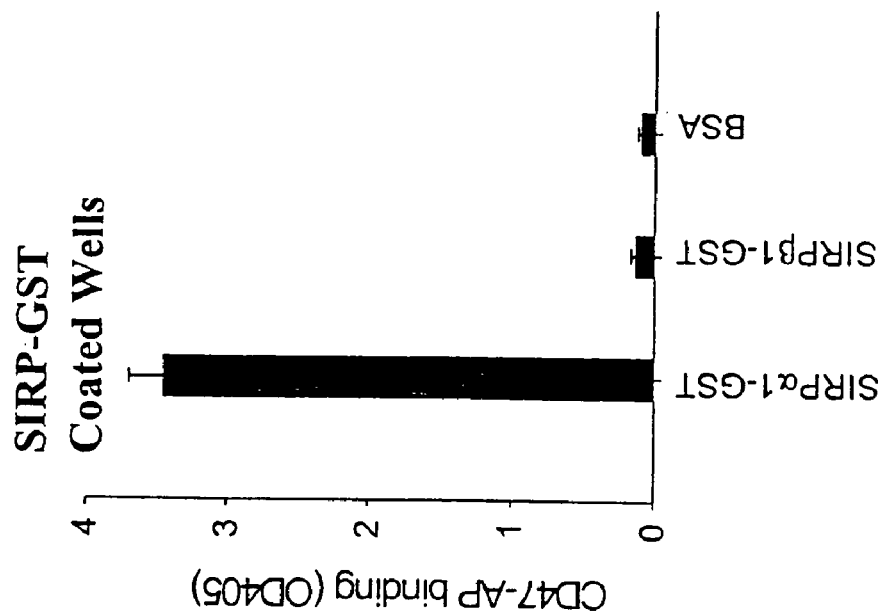
FIG. 2B (left panel) is a bar graph that illustrates the direct binding of SIRPα1-GST to the extracellular IgV loop of CD47 (CD47-AP) which is inhibited by SIRPα and CD47 mAbs. In this panel, microtiter wells were coated with recombinant CD47 (10 µg/ml) consisting of the extracellular IgV loop of CD47 fused to human alkaline phosphatase followed by blocking with BSA. As a control, wells were also coated with a similar recombinant protein consisting of the extracellular IgV loops of JAM (Junctional Adhesion Molecule) fused to alkaline phosphatase (JAM-AP). SIRPα1-GST was then added to the wells in the presence or absence of anti SIRP (P3C4, SE5A5) or anti CD47 (C5/D5) followed by color development after addition of peroxidase conjugated goat anti GST as detailed for FIG. 2A.
Figure 2C:
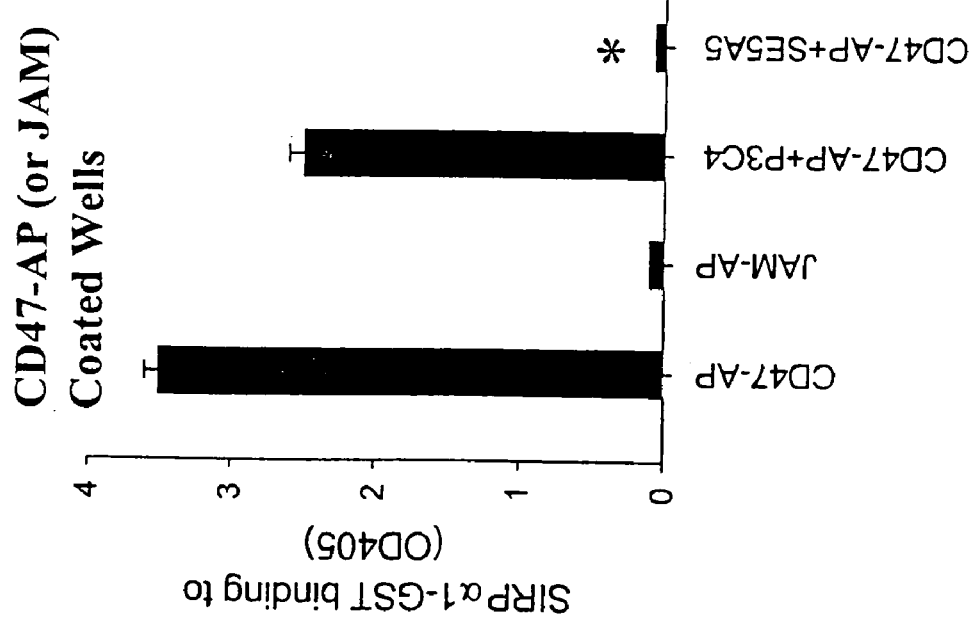
FIG. 2C (right panel) is a bar graph that illustrates CD47-AP specifically binds to SIRPα-GST fusion protein but not SIRPβ-GST. In this panel, microtiter plates were coated with either SIRPα-GST or highly similar SIRPβ-GST (10 µg/ml) followed by blocking with BSA. To each well was then added recombinant CD47-AP followed by washing. Bound CD47-AP was then detected by assay for alkaline phosphatase after addition of appropriate substrate.

Since the above results and those of others (Jiang, et al *J. Biol. Chem.*, 274: 559, Seiffert, et al., *Blood,* 94: 3633, Han, et al., *J. Biol. Chem.,* 275: 37984, Oldenborg, et al., *Science,* 288: 2051) strongly implicate CD47 as a membrane receptor for SIRPα, experiments were performed to test the direct binding of the IgV loop of CD47 to SIRPα (FIG. 2B). A recombinant CD47 IgV loop fused to alkaline phosphatase (CD47-AP) was constructed as detailed in the methods and expressed in mammalian (CHO) cells in order to allow for proper folding and glycosylation. The expressed CD47-AP fusion protein was then purified by immunoaffinity chromatography using anti CD47 mAb PF3.1-Sepharose. The structure of CD47 IgV domain in the purified CD47-AP was further tested for the ability to react with multiple functionally blocking anti-CD47 extracellular domain-reactive mAbs (Liu, et al., *J. Biol. Chem.,* 276: 40156). To assay CD47-AP binding to SIRPα1, microtiter plates were coated with SIRPα-GST (2 µg/ml), blocked with BSA, followed by incubation with CD47-AP (1-2 µg/ml). Binding of CD47-AP was then assayed by directly measuring alkaline phosphatase (AP) activity. Conversely, wells coated with CD47 or JAM-AP were also assayed for binding with SIRP-GST using appropriate secondary antibodies. As shown in FIG. 2C, CD47-AP bound to SIRPα-GST fusion protein resulting in a high value of AP activity (OD405). Specificity of this interaction was confirmed by the absence of binding of the control AP fusion protein containing the extracellular domain of junction adhesion molecule (JAM-AP) (Liu, et al., *Journal of Cell Science,* 113: 2363) and the lack of binding to either SIRPβ-GST or BSA or when inhibitory anti-SIRP or CD47 mAbs were added (SIRP mAb SE5A5, CD47 mAb C5/D5). These results indicate that CD47 binds directly and specifically to SIRPα via the extracellular IgV domain of CD47.

Figure 3:
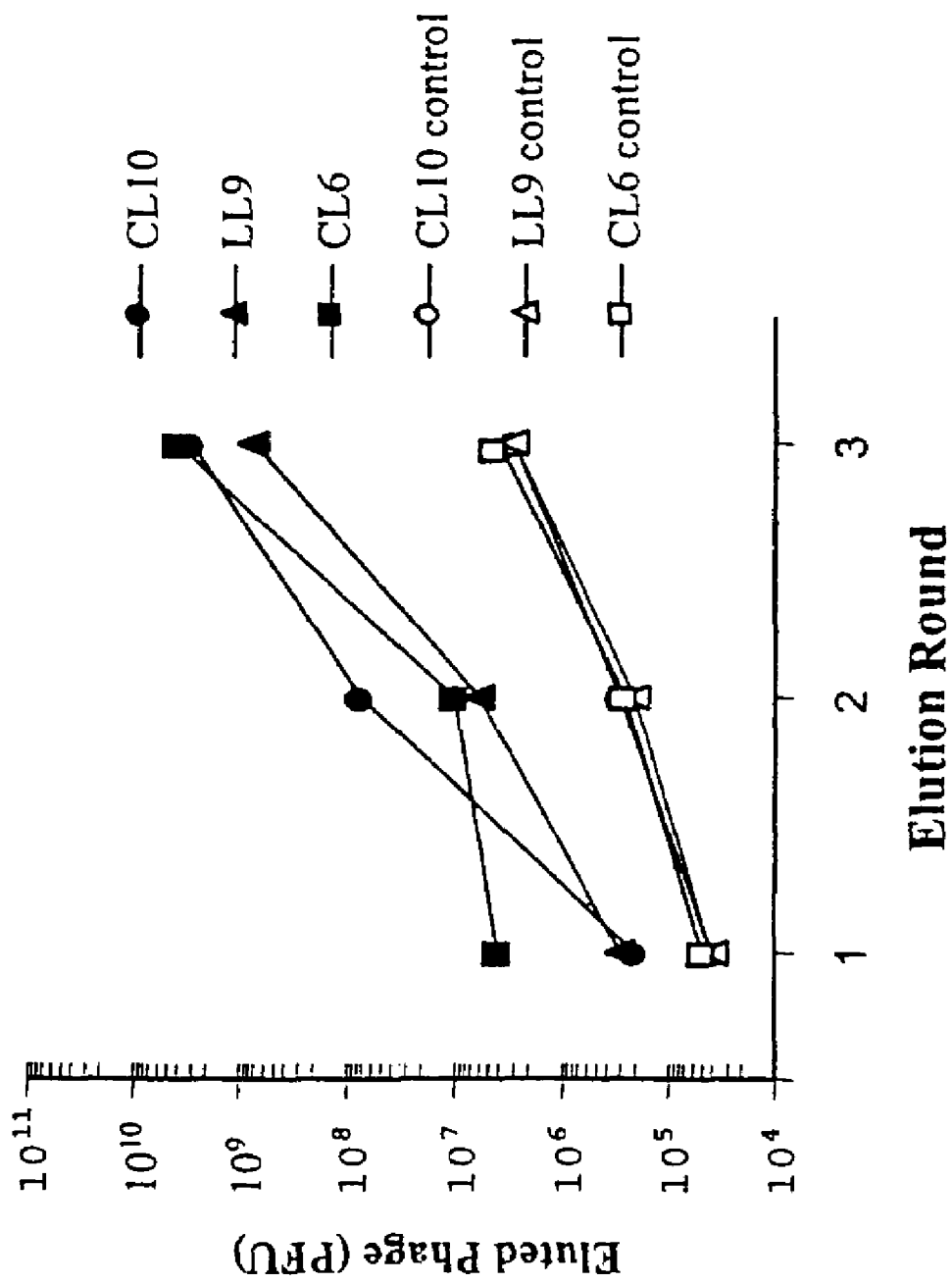
FIG. 3 is a graph that illustrates the amplification of selected phage from CL10, LL9 and CL6 phage display libraries through three rounds of panning with mAb C5/D5 conjugated to Sepharose and control unconjugated beads. C5/D5-conjugated beads were incubated with random decapeptide CL10 library ( ), hexapeptide CL6 library ( ) and nonapeptide J404 library ( ). Control unconjugated beads were also incubated with CL10 ( ) CL6 ( ) and J404 ( ) as controls. After a thorough wash, phages that bound to antibody conjugated and unconjugated Sepharose were eluted at pH 2.2 and the numbers were titrated by counting plaque forming units on E coli K91 containing agar plates as described in experimental procedures below.

Identification of Anti-CD47 mAb C5/D5 Binding Peptide Sequences Using Phage Display Libraries Since mAb C5/D5 potently inhibited CD47-SIRPα interactions (FIG. 2A-2C), phage display libraries were panned over C5/D5-sepharose in order to identify the amino acid sequences that are potentially involved in CD47-SIRPα interactions. Three different phage display libraries were used in the panning, one linear nona-peptide (LL9) and two cysteine constrained hexa- and deca-peptide (CL6 and CL10 respectively) libraries in which the random peptide sequences were constrained to form loops as a result of disulfide bond formation between flanking cysteine residues. Where as in LL9, the peptides were displayed in a linear fashion without disulfide bonds. Three rounds of antibody panning and amplification were performed to select phage baring C5/D5-binding peptide sequences. As shown in FIG. 3, an increase of approximately four logs of CL10 phage binding to C5/D5, three and half logs for LL9 phage and three logs for CL6 were obtained after panning, indicating increasing numbers of phage that specifically bound to C5/D5. In contrast, an increase of only two logs was obtained with CL10, LL9 and CL6 phage that panning using control Sepharose with no coupled antibody (FIG. 3). Phage that bound to C5/D5-Sepharese obtained after three rounds of panning were further selected by plaque-lift assays followed by western blot analysis (described in the Experimental Procedure herein). In these assays, phage plaques formed on *E.coli* K91 containing LB-agar were duplicated to nitrocellulose followed by blotting with mAb C5/D5, a procedure similar as antibody western blot. A total of 80 positive C5/D5-binding phage were selected from structurally constrained phage libraries CL10 and CL6. However, for structurally linear phage library LL9, no positive clone was observed by plaque-lift assays. Thus, 10 phage from the agar plates were chosen. The individual phage were amplified, isolated and DNA sequenced. The deduced amino acid sequences are presented in Table 4. As shown in Table 4, 15 phage sequences were recovered from 60 positive C5/D5-binding CL10 phage with 5 phage sequences recovered more than once (for example, phage C5/D5.1 was recovered six times, etc.). 10 phage sequences were obtained from CL6 library out of total 20 phage sequenced (Table 4). The 10 randomly selected LL9 phage only yielded two sequences with one sequence repeated 15 times and other one 5 times. Table 4 also indicates that approximately 40% of the selected CL6 phage had lost either the 5' or 3' cysteine residue flanking the random region in their sequences. In almost 80% of such cases the change was due to a single C→G base pair mutation (TGC→TGG) resulting in a cysteine to tryptophan change. In the remaining cases, the mutation found was TGC→TCC, which resulted in a cysteine switch to serine. In all such cases where the 5' or 3' cysteine was missing, an additional cysteine residue was displayed within the random region suggesting that a constrained peptide conformation could formed and such conformation may be important for binding to the antibody C5/D5.

TABLE 4*

| Panning Selected Phages | | Binding To C5D5 (by ELISA) | Peptide Synthesized | |
|---|---|---|---|---|
| | | | Name | Solubility |
| From CL10 library: | | | | |
| CERVIGTGWVRC (×6) | SEQ ID NO: 2 | Strong binding | C5D5.1 | 10 mM |
| CHRVPGHGWVRC (×5) | SEQ ID NO: 6 | Strong binding | C5D5.12 | 1.0 mM |
| CSWQHQDGWVWC | SEQ ID NO: 10 | Strong binding | | |
| CVPVCREGWCGC | SEQ ID NO: 11 | Not tested | | |
| CYKSMDGWVVPC | SEQ ID NO: 12 | Strong binding | | |
| CVENVDGWTVPC (×2) | SEQ ID NO: 13 | Strong binding | | |
| CRVPETGWVKC | SEQ ID NO: 14 | Not tested | | |
| CRLMLNGWVVPC | SEQ ID NO.: 15 | Not tested | | |
| CCRDGWCHHDWC | SEQ ID NO: 16 | Strong binding | | |
| CCREGWCGDGLC | SEQ ID NO: 17 | Not tested | | |
| CGWRNSFGQSLC (×32) | SEQ ID N.: 8 | Strong binding | C5D5.2 | |
| CGWRNALGQVVC | SEQ ID NO: 18 | Not tested | | |
| CGWRNLEGGSVC | SEQ ID NO: 19 | Not tested | | |
| CGWRDDSGQSMC | SEQ ID NO: 20 | Not tested | | |

TABLE 4*-continued

| Panning Selected Phages | Binding To C5D5 (by ELISA) | Peptide Synthesized Name | Solubility |
|---|---|---|---|
| CRRVIGRVGCGC SEQ ID NO: 4 | Strong binding | C5D5.3 | |
| From CL6 library | | | |
| WCRGGWC (×4) SEQ ID NO: 21 | Strong binding | | |
| WCKSGWC (×2) SEQ ID NO: 22 | Strong binding | | |
| CLCAEGWC (×4) SEQ ID NO: 23 | Strong binding | | |
| CHPGTGWC (×3) SEQ ID NO: 24 | Strong binding | | |
| SYCREGWC SEQ ID NO: 25 | Modest binding | | |
| CGCRDGWC SEQ ID NO: 26 | Modest binding | | |
| CLCHGGWC SEQ ID NO: 27 | Modest binding | | |
| WCVKGWC SEQ ID NO: 28 | Not tested | | |
| CRDGWCYS SEQ ID NO: 29 | Not specific | | |
| CVAILKDC SEQ ID NO: 30 | No binding | | |
| From LL9 library: | | | |
| GWPRVGFRL (×15) SEQ ID NO: 31 | Strong binding | | |
| GLVKDAGFF (×5) SEQ ID NO: 32 | No binding | | |
| Controls peptides for C5D5.1: | | | |
| ERVIGTGWVR SEQ ID NO: 34 | | C5D5.4 | 10 mM |
| CGVRTWRGVIEC SEQ ID NO: 35 | | C5D5.5 | 2 mM |
| CHRVIGTGWVRC SEQ ID NO: 36 | | C5D5.11 | 10 mM |

*Peptide sequences obtained from panning C5D5 with cysteine constrained (CL10 and CL6) and linear (LL9) phage display libraries. The linker sequence at the carboxyl end of the random region (GPP, not shown) was correctly displayed in all clones. Many of the CL6 phage contained a single base pair mutation resulting in a change of amino terminal cysteine to tryptophan. In all cases where the 5' cysteine was missing, an additional cysteine was displayed within the random region. Table 4 also lists the ability of these phages directly binding to mAb C5D5 after isolation. Consensus residues are in bold. Sequences that are selected to synthesize peptides are named and their solubility in aqueous phase are presented.

Analysis of C5/D5-Binding Phage Sequences

Figures 4A, 4B:
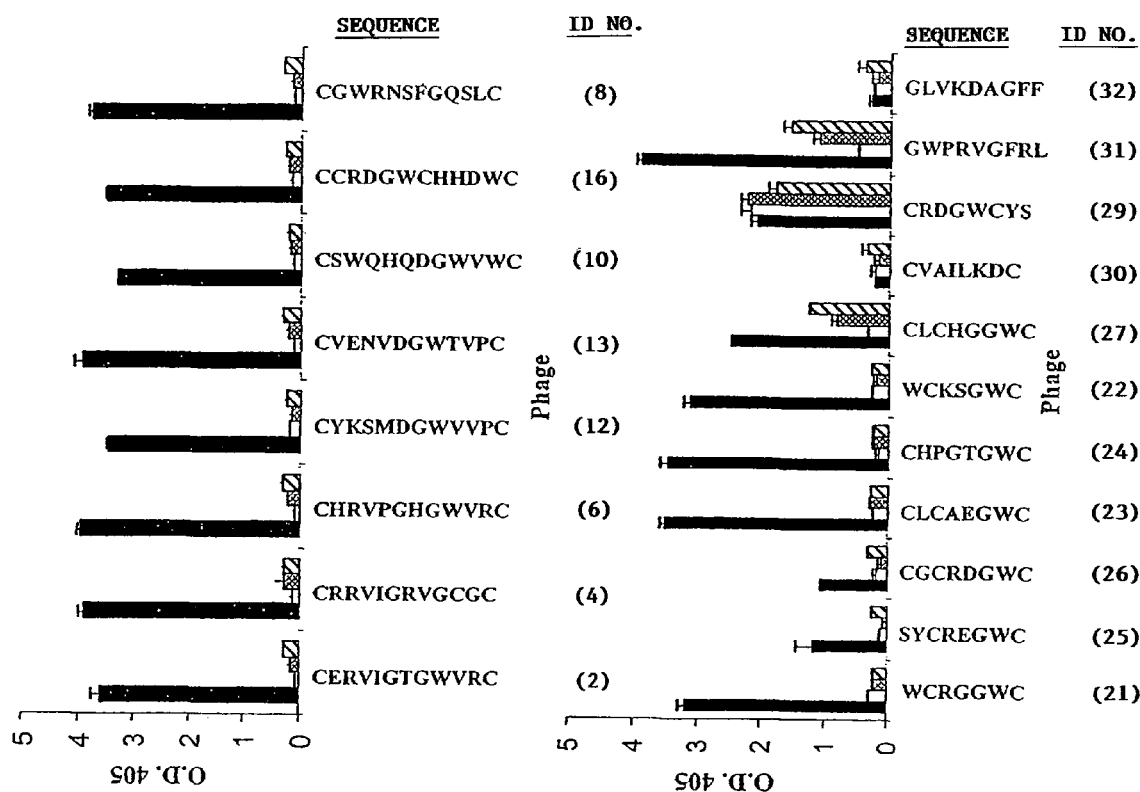
FIGS. 4A and 4B are graphs that illustrate reactivity of selected peptide-bearing phage clones by ELISA with antibodies C5D5 (solid bars), B6H12 (white bars), PF3.1 (hatched bars) and IgG1 (striped bars).

Analysis of the C5/D5 selected phage sequences in Table 4 revealed two major consensus sequences: CXR(VXX)[D/E/N/T]GW[V/C]R/(X)(X)(X)C (SEQ ID NO:47) (only one residue can reside between "[]", "/" means "or" so that those residues are interchangeable; residues in ( ) are either present or absent, X represents any variable residue) (i.e., CXRVXXXGWVRC, SEQ ID NO:46) and CGWRNXXGQS[V/L]C (SEQ ID NO:48) from CL10. Only one CL10 phage sequence CRRVIGRVGCGC, SEQ ID NO:4, has no GW consensus. A consensus sequence C[R/X][E/D/T/G]GWC, (SEQ ID NO:49), which resembles to the first consensus motif of CL10 phage sequences, was obtained from CL6 phage. These sequence consensus studies provide the first clue of mAb C5/D5 binding motif, suggesting that certain amino acids may required to form an antigen epitope for antibody binding. To further test these phage (in Table 4) that are these consensus sequences in binding to mAb C5/D5 and to examine their binding specificity, direct phage-antibody binding by ELISA were performed after propagation and isolation of each individual phage. Phage in the CL10 and CL6 that display unique peptide motifs were selected. As shown in FIG. 4A, all CL10 phage selected bound to C5/D5 and not to other anti-CD47 mAbs B6H12, PF3.1, or to isotype control IgG1 (FIG. 4A). From CL6, seven of the nine selected phage bound specifically to C5/D5 (FIG. 4B and Table 4). Although all of these CL10 and CL6 phage bound to C5/D5, the amount of CL6 phage used were approximately 10-100 fold higher than those for CL10 phage in order to obtain reasonable binding results, indicating that CL6 phage had lower affinity for the antibody. Since those positive CL6 phage contain the similar amino acid motifs as for CL10, such as G(T)GW and charged residues R/E/H in the sequences, it is likely that these residues are important for C5/D5 binding although higher affinity binding requires additional residues. In contrast, CL6 phage bearing the peptide sequence CRDGW-CYS (SEQ ID NO:29), which has an extra "Y" after GWC, lost binding specificity and bound to all antibodies tested. Phage bearing the sequence CVAILKDC (SEQ ID NO:30), which contain no GW residues, did not bind any of the antibodies tested. Two dominant sequences of LL9 phage were also tested and it was found that the phage bearing the sequence GWPRVGFRL (SEQ ID NO:31) bound to C5/D5 while phage bearing the sequence GLVKDAGFF (SEQ ID NO:32) did not bind as tested by ELISA (FIG. 4B). As indicated by Table 4, this C5/D5-binding phage "GWPRVG-FRL" (SEQ ID NO:31) contains the motifs GWXRV, GW and RV, which were also prominently displayed in the sequences isolated from CL10 and CL6 libraries, further emphasizing the importance of those consensus residues in C5/D5 binding. Table 4 also summarized the binding properties of these phage to mAb C5/D5.

Peptide C5/D5.1 Competitively Inhibits CD47-C5/D5 Binding

Figure 5:
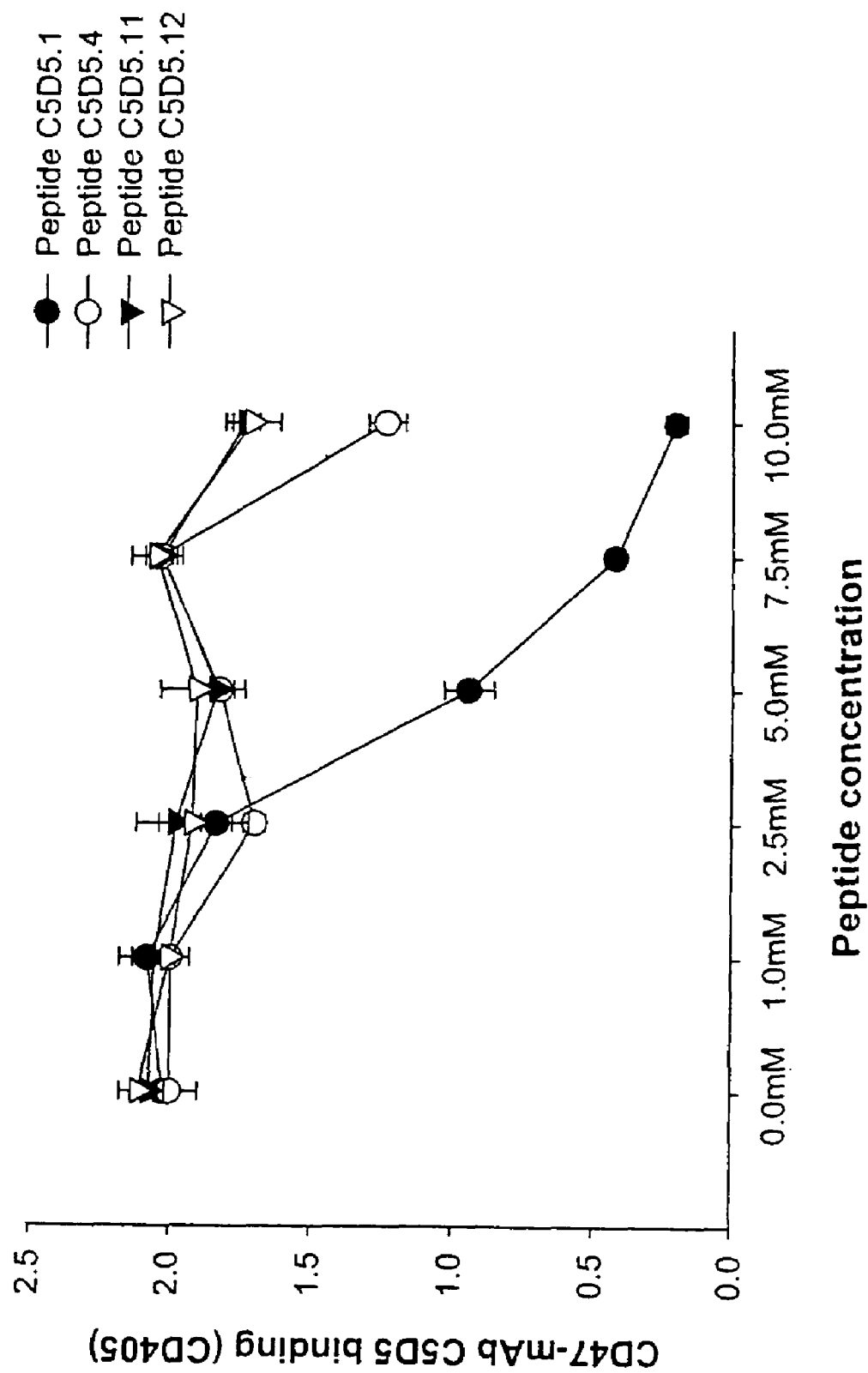
FIG. 5 is a graph that illustrates the effect of synthetic peptide C5/D5.1 (CERVIGTGWVRC) (SEQ. ID NO: 2) and control peptide C5/D5.4 (ERVIGTGWVR) (SEQ. ID NO: 34), C5/D5.11 (CHRVIGTGWVRC) (SEQ. ID NO: 36) and C5/D5.12 (CHRVPGHGWVRC) (SEQ. ID NO: 6) on binding of C5/D5 Fab to CD47. CD47 was purified from human PMN or RBC as previously described (Liu, et al., Journal of Biological Chemistry, 277(12): 10028-36, 2002). The experiments were performed by coating microtiter plates with purified CD47 (in 1% octylglucoside containing buffer, used as 1:50 dilution) for 2 hour (hr). After blocking, C5/D5 Fab (1 µg/ml) was added without or with increasing amount of peptides. C5/D5 Fab binding was detected by a peroxidase conjugated goat anti-mouse secondary antibody. The data represent the mean and the standard deviation of triplicate wells.

To confirm that peptide C5/D5.1 simulates the natural epitope of CD47 recognized by mAb C5/D5, experiments were performed to test if this peptide can compete with CD47 in binding to C5/D5. Purified human CD47 from PMN and RBC was used to coat microtiter plates followed by incubation with C5/D5 Fab (1 μg/ml) either in the absence or presence of increasing amount C5/D5.1 or other control peptides. As shown in FIG. 5, peptide C5/D5.1 competitively inhibited C5/D5 Fab binding to CD47 with $IC_{50}$ of 3.8 mM. In contrast, control peptides, including C5/D5.11 (SEQ ID NO:36) and C5/D5.12 (SEQ ID NO:6) had no inhibition at concentrations up to 10 mM (FIG. 5). Another control peptide C5/D5.4 (SEQ ID NO:34), which contains the core amino acid sequence of C5/D5.1 but without cysteines to impose structural constraint, displayed no inhibition in CD47-antibody binding except at concentrations greater than 10 mM. Scrambled control peptide C5/D5.5 (SEQ ID NO:35) was used in the experiments. This peptide had no effect on CD47-antibody binding up to 2 mM (data not shown, this peptide was not synthesized further due to its limited solubility). From these competitive binding results, it was concluded that peptide C5/D5.1 imitates the C5/D5 binding epitope on CD47. Since this sequence is not present in the linear sequence of CD47, it is postulated that C5/D5 recognizes an epitope containing residues from the tertiary structure (discontinuous in nature) on the CD47 protein surface.

Peptide C5/D5.1 Directly Binds to the Extracellular Domain of SIRPα1

Figure 6B:
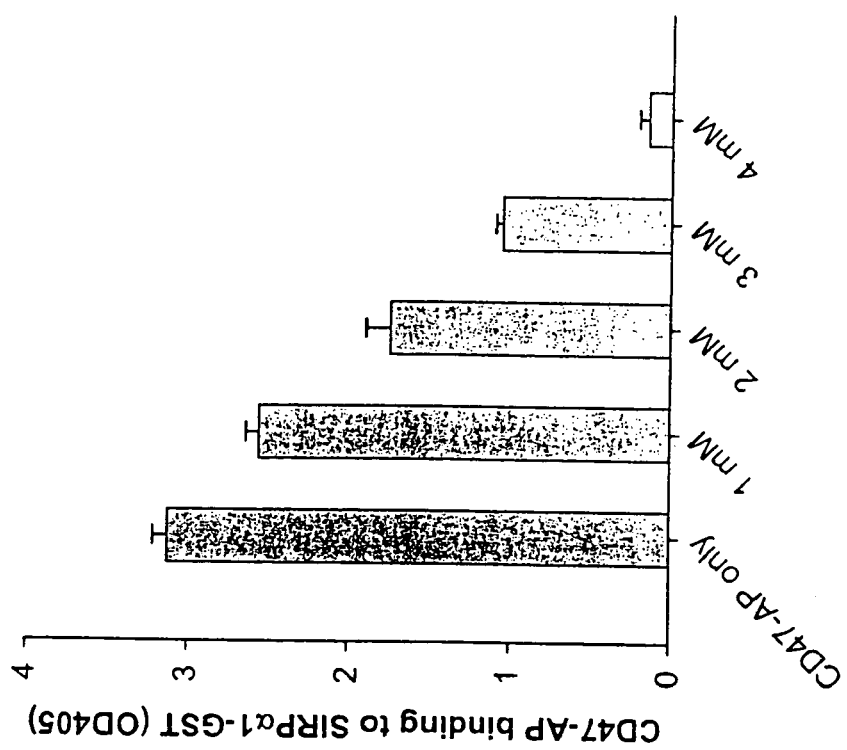
Figure 6A:
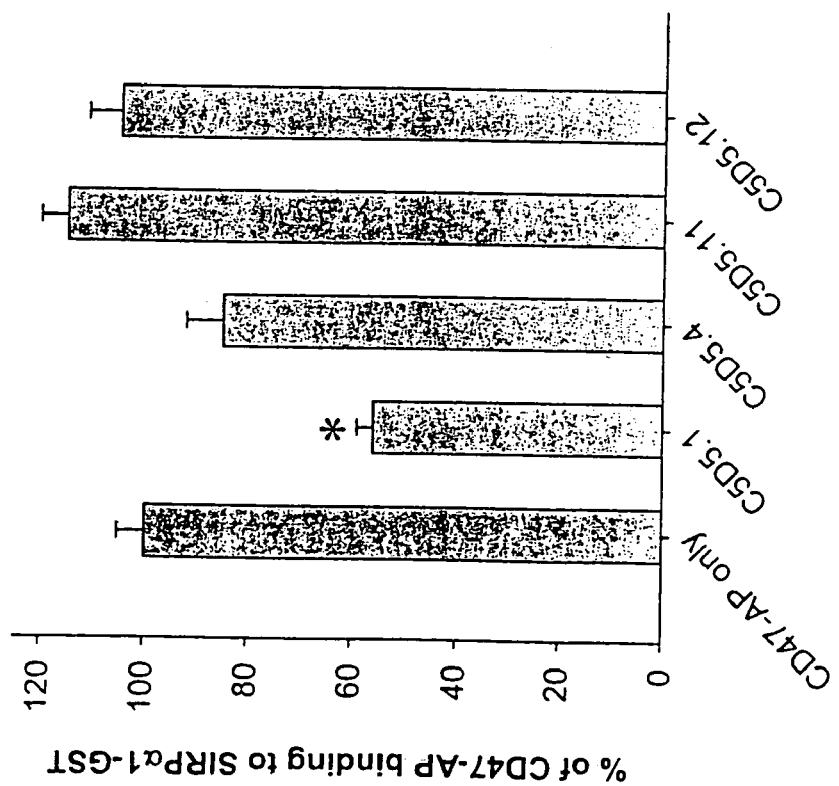

Previously mAb C5/D5 was shown to inhibit CD47-SIRPα1 binding by blocking a functional epitope on the CD47 extracellular domain. This suggests that the C5/D5 epitope on CD47 directly mediates, in part, CD47-SIRPα binding. Experiments were conducted to examine this hypothesis by testing the effect of peptide C5/D5.1 in CD47-SIRPα binding. In vitro CD47-SIRPα binding experiments were conducted using the extracellular domain recombinant proteins of SIRPα1 (SIRPα1-GST) and CD47 (CD47-AP) in which SIRPα1-GST fusion protein was immobilized and its binding to CD47 was assessed by incubation with CD47-AP followed by assaying alkaline phosphatase activity (Liu, et al. *J. Biol. Chem.*, 277(12): 10028-36, 2002). Although CD47 and SIRPα used in the assay are both recombinant fusion proteins, we have previously demonstrated that CD47-AP and SIRPα1-GST binding is mediated by interactions between CD47 and SIRPα1. To examine whether peptide C5/D5.1 could interfere CD47-SIRPα binding, binding assays were performed in the absence or presence of peptide C5/D5.1 and control peptides. As shown in FIG. 6A, control peptides C5/D5.4, C5/D5.11 and C5/D5.12 (each used at 2 mM) demonstrated no inhibition of CD47-AP (1 µg/ml) and SIRPα1-GST (coated at 1 µg/ml) binding compared to controls (CD47-AP only). On the contrary, same concentration of peptide C5/D5.1 partially inhibited CD47-AP binding to SIRPα1-GST. FIG. 6B demonstrates that peptide C5/D5.1 inhibited CD47-SIRPα1 binding in a dose-dependent manner. As shown, in the presence of 4 mM peptide C5/D5.1, the binding of CD47-AP with SIRPα1-GST was completely abrogated. These results indicate that C5/D5.1 markedly inhibits CD47-SIRPα binding in a specific fashion and suggest that peptide C5/D5.1 may bind to SIRPα1.

Next, peptide C5/D5.1 was immobilized on micro titer plates and tested for direct binding to CD47-AP and SIRPα1-GST. As shown in FIG. 6C, peptide C5/D5.1 directly binds to SIRPα1 fusion protein, but not CD47-AP or other control proteins (BSA). Thus, these results indicate that peptide C5/D5.1 contains an amino acid sequence that represents, in part, the CD47 binding epitope for SIRPα. Since the concentration of peptide C5/D5.1 (1-4 mM) used to compete with CD47 in binding to SIRPα1 was over three logs more than that of CD47-AP (about 0.8 µM), it is likely that peptide C5/D5.1 represents a lower affinity binding sequence that may require additional residues to increase affinity in binding to SIRPα1. Since the three dimensional structure of CD47, SIRPα and their binding interaction are not known, our results provide the first clues as to which residues on CD47 may be involved in binding to SIRPα.

Peptide C5/D5.1 Inhibits PMN Transepithelial Migration

Figure 7A:
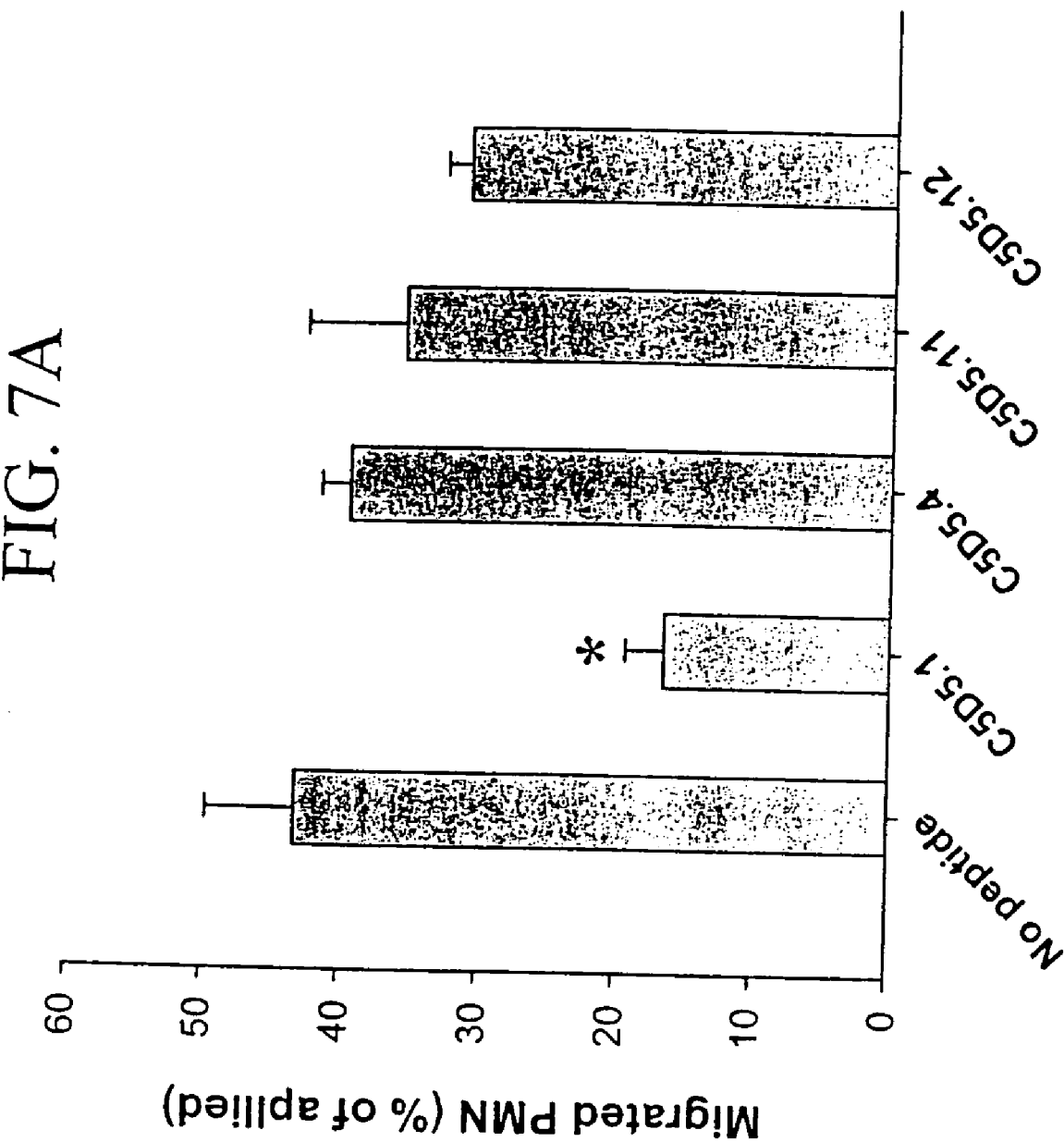

Previously it was demonstrated that CD47-SIRPα interactions play an important role in regulating PMN migration. The functional significance of peptide C5/D5.1 in PMN transmigration was tested using a transwell migration setup (Parkos, et al., *J. Cell Biol.*, 132(3): 437-50, 1996; Liu, et al., *J. Biol. Chem.*, 276(43): 40156-66, 2001; Liu, Y., et al., *J. Biol. Chem.*, 277(12): 10028-36, 2002). In the experiments, fresh isolated PMN ($10^6$) were pre-incubated with 0.5 mM peptide C5/D5.1 and the control peptides C5/D5.4, C5/D5.11 and C5/D5.12 (0.5 mM of each) before use in transmigration assays. PMN migration was induced migration across collagen-coated filters from the upper chamber towards the chemoattractant fMLP containing lower chamber in the transwell setup. PMN migration into the lower chamber was then quantitated by MPO assay (Parkos, et al., *J. Cell Biol.*, 132(3): 437-50, 1996). As shown in FIG. 7A, compared to non-peptide treatment control in which 43.4±6.1% of total applied PMN transmigrated after 2 hr incubation, in the presence of 0.5 mM of peptide C5/D5.1 PMN transmigration decreased to 16.3±2.3% after the same incubation. In contrast, the same concentrations of control peptides C5/D5.4, C5/D5.11 and C5/D5.12 (0.5 mM of each) did not significantly affect PMN migration (39.2±3.1%, 35.4±7.8% and 32.3±2.5% migrated in the presence of C5/D5.4, C5/D5.11 and C5/D5.12, respectively) after 2 hr incubation. FIG. 7B shows the dose-dependence of inhibition of migration by peptide C5/D5.1. As can be seen, in this 1 h migration assay, peptide C5/D5.1 displayed partial inhibition in PMN transmigration at concentrations as low as 0.1 mM. Migration was progressively inhibited when peptide concentrations were increased to 0.25 mM and was virtually abolished after peptide C5/D5.1 concentrations 1 mM or greater. In the same migration assay, however, control peptide C5/D5.4 demonstrated only partial inhibition at concentrations greater than 2 mM (FIG. 7C). Similar inhibition profiles by peptide C5/D5.1 were observed when the assays were performed using confluent monolayers of T84 intestinal epithelial monolayers (data not shown).

Discussion of Results from Example 1

Recombinant CD47 extracellular IgV domain and alkaline phosphatase (AP) fusion protein directly bound to SIRPα1 extracellular domain and GST fusion protein in vitro (Liu, Y., et al., *J Biol Chem* 277(12): 10028-36, 2002) has been shown. Also, CD47-AP bound to SIRPα1-GST via interactions of their extracellular Ig domains (Liu, Y., et al., *J. Biol. Chem.*, 277(12): 10028-36, 2002) has been demonstrated. Amino acids on CD47 that mediate CD47-SIRPα binding are identified. There are limited approaches that can be taken currently to identify exact amino acids on proteins that involved in protein-protein interactions without structural information. Initially site-directed mutagenesis was performed to define the essential residues on CD47 extracellular domain. While mutagenesis is a standard method for structural/functional analysis, such studies on CD47 carried out by transcient expression of epitope-tagged mutated CD47 DNA constructs in COS-1 cells have been inconclusive. For example, the highly conserved "invariant" tryptophan ($W^{58}$) (Vaughn, et al., *Neuron* 16(2): 261-73, 1996; Chothia, et al., *Annu. Rev. Biochem.*, 66: 823-62, 1997) to alanine within the putative IgV-like domain appears to obliterate expression of the mutated CD47, suggesting that certain amino acids may be critical for initial protein folding during expression.

In these experiments, random peptide phage display was used to identify peptides that bind to CD47 mAbs and hence provide structural information on functional epitopes on surface of CD47. Initially, the entire putative extracellular IgV loop of CD47, SEQ ID NO:9, (residues C41-C114) was constructed and bound to the N-terminus of pIII as a 222 base pair insertion and it was found that phage expressing the entire CD47 putative extracellular loop demonstrate a six-fold increase in binding to mAb C5/D5 compared to wild type phage (data not shown). However, mAb C5/D5 failed to recognize such phage under more stringent binding conditions (western blot). Then three M13 phage display libraries displaying short linear and structurally constrained peptide sequences were used to pan on C5/D5-Sepharose. Since mAb C5/D5 abrogates CD47-SIRPα binding, the C5/D5 epitope may represent, in partial, a functional domain on CD47. Preliminary panning using the linear nona-peptide phage display library J404 (same as LL9) on C5/D5-sepharose did not yield peptide sequence motifs that clearly bound to C5/D5. Subsequent plaque-lift assays of phages eluted from C5/D5-Sepharose did not detect any positive reaction with C5/D5 on nitrocellulose. While, the amino acid sequences deduced from primary DNA sequencing from C5/D5-Sepharose eluates indicated that several regions within the CD47 IgV loop might be interesting. These regions correspond to four different positions of CD47 (SEQ ID NO:9) extracellular domain including residues KWK-FKGRD (aa57-64 of SEQ. ID NO:9), SSAKIEVSQLLK (aa82-93 of SEQ. ID NO: 9) and GDASLKMDK (aa94-102 of SEQ. ID NO: 9) and EVTELTREG (aa115-123 of SEQ. ID NO: 9) (data not shown). Linear peptides comprising these segments of CD47 were synthesized and tested in directly binding to mAb C5/D5 and SIRPα1-GST. However, these peptides displayed only weak binding (KWK-FKGRDIYT (aa57-67 of SEQ. ID NO: 9) and GDASLK-MDKS aa94-103 of SEQ. ID NO: 9) or no binding to either C5/D5 or SIRPα1-GST (data not shown).

The panning results with the linear phage library (LL9) suggest that the functional domain on CD47 that bind to mAb C5/D5 exists as a unique tertiary structure that can not be represented by a linear peptide. In support of this, mAb C5/D5 has been shown to only recognize non-denatured and non-reduced CD47. Thus, panning experiments were performed using two structurally constrained hexa- and decapeptide (CL6 and CL10) to increase the chances of identifying peptide motifs that bind to C5/D5. After multiple rounds of panning on C5/D5 with these peptide libraries, amino acid motifs that bound to mAb C5/D5 (Table 4) were identified. Although panning with LL9 library yielded one C5/D5-binding sequence, which remains some uncertainty because phage containing this sequence did not react with C5/D5 in plaque-lift assay. All other C5/D5 binding sequences were produced from structurally constrained peptide libraries CL10 and CL6, suggesting that the constrained structures of the displayed peptides are essential for binding. The importance of Cys residues imposed tertiary structures in CL10 and CL6 phages were further confirmed after disruption of disulfide bonds with the reducing reagent DTT. In the presence of 10 mM DTT, CL10 and CL6 phage binding to C5/D5 were eliminated (data not shown).

None of the C5/D5-selected phage bound to other anti-CD47 mAbs B6H12 and PF3.1 or to isotype control IgG1 indicating that these phages are bind specifically unique regions on the C5/D5 antibody. Furthermore, panning experiments performed with Abs B6H12, PF3.1 and IgG using LL9, CL6 and CL10 phage libraries yielded very different sequence motifs to those obtained with C5/D5 and phages bearing these different sequences did not bind to C5/D5 by ELISA. From panning against C5/D5, two groups of peptide sequences containing structurally constrained consensus motifs, CXR(VXX)[D/E/N/T]GW[V/C]R/(X)(X)(X)C (SEQ ID NO:47) and CGWRNXXGQS[V/L]C (SEQ ID NO:48) from CL10 library, which bind to mAb C5/D5 were obtained (Table 4). One consensus motif CR/XE/D/T/GGWC was obtained from CL6 library, which resembles the motif from CL10 library. A striking finding was that amino acids GW were present in all but one of the phages that bind to C5/D5 (Table 4).

Three sequences were chosen and contained consensus motifs derived from positive CL10 phages to synthesize peptides (Table 4), based on that CL10 phages tend to have higher affinity in binding with mAb C5/D5 than CL6 phages suggesting that the C5/D5 epitope likely comprises more than six amino acids. To mimic the possible constrained structure in phage, in vitro oxidation was performed after peptide synthesis to introduce disulfide bonds between Cysteine residues in these peptides. A peptide containing one of these motifs was found, C5/D5.1 displays high affinity in binding with mAb C5/D5 and effectively competed all of the C5/D5-selected CL10 and CL6 phages binding to C5/D5 at concentrations in the low μM range by ELISA. Another peptide C5/D5.2, SEQ ID NO:8, (CGWRNSFGQSLC), however, only competed CL10 and CL6 phages binding at high concentration (mM range). There were no inhibitory effects of peptide C5/D5.3, SEQ ID NO:4, (CRRVI-GRVGCGC) up to 10 mM. C5/D5.3 is the only sequence that has no trptophan (W) but bound to C5/D5. Failure of this peptide in competition assays with other C5/D5-binding phages indicates this sequence to be a low affinity binding target for mAb C5/D5, thus further demonstrating the important role of tryptophan (W) in peptide binding. There are total four tryptophan (W) residues in CD47. W2 is part of the signal peptide and therefore is not present in the mature protein. W58 is present in the N-terminus extracellular IgV-like domain of CD47 and is conserved among many IgV super family members. W136 is also located in the putative extracellular domain whereas W157 is thought to be in a transmembrane region of the protein (Lindberg, et al., *J. Cell Biol.*, 123(2): 485-96, 1993). Amino acids Arginine and Valine (RV/L), present in many selected CL10 and LL9 phages are adjacent in CD47 at amino acid position 132-133, two amino acids upstream from W136. Both amino acids R and V are also found close to W58. Thus, the C5/D5-binding sequence on CD47 is likely to comprise several distant residues brought into proximity by the folding of the protein.

The high affinity C5/D5-binding peptide C5/D5.1 (CERVIGTGWVRC) was further studied. This peptide was found to compete with native CD47 in binding with C5/D5 in ELISA demonstrating that it contains sequence that may partially mimic the C5/D5 epitope. The relatively high concentration of the peptide C5/D5.1 required to inhibit C5/D5-CD47 binding ($IC_{50}$ 3.8 mM) may be due to incomplete optimization of the residues and structure. The epitope on CD47, which is discontinuous and present in the tertiary structure may be difficult to mimic by a short peptide. Despite this issue, the inhibitory concentrations for C5/D5.1 are comparable to those reported in other epitope mapping studies using hexapeptide and heptamer peptides (Chen, et al. *Proceedings of the National Academy of Sciences of the United States of America* 93(5), 1996: 1997-2001; Birkenmeier, et al., *FEBS Letters* 416(2): 193-6, 1997). Despite this limitation, the concentrations of C5/D5.1 used in these experiments are comparable to those of RGD containing peptides to inhibit cell binding to fibronectin- or vitronectin-coated plates (Pasqualini, et al., *J. Cell Biol.*, 130(5): 1189-96, 1995).

Not only did peptide C5/D5.1 compete CD47 binding to mAb C5/D5, it also successfully competed CD47 binding to its extracellular ligand SIRPα. FIGS. 7A-7C show that peptide C5/D5.1 dose-dependently inhibited CD47-SIRPα1 binding, indicating the specificity of this peptide. Furthermore, peptide C5/D5.1 inhibited CD47-SIRPα1 interaction by directly binding to SIRPα1 (FIG. 6C). Since peptide C5/D5.1 mimics the CD47 epitope for inhibitory anti-CD47 mAb C5/D5, the peptide-SIRPα interaction is likely mediated in a fashion similar to the interaction between CD47-SIRPα. Previously, studies demonstrated that an extracellular domain soluble form of CD47 fusion protein (CD47-AP) inhibited PMN transmigration through interactions with cell surface SIRPα. In this study, peptide C5/D5.1 does-dependently inhibited PMN transmigration. This result further implies that this peptide represents, in part, the SIRPα functional binding epitope on CD47. However, compared to CD47, the natural ligand for SIRPα, peptide C5/D5.1 likely represents a lower affinity binding partner for SIRPα. The sequence information obtained in this study provides valuable structural information about the interactive regions on the CD47 protein. The fact that peptide C5/D5.1 is not exist as a linear sequence on the CD47 primary structure has confirmed our hypothesis that the three dimensional structure of the protein is required for binding and function. Further studies are necessary by employing protein modeling techniques to further define the structure of this peptide in order to improve its binding affinity.

Experimental Procedures for Example 1

Antibodies

Three anti-CD47 mAbs C5/D5, B6H12 and PF3.1 were used and all were IgG1 isotype. C5/D5 was developed in this laboratory and has been previously characterized (Parkos, et al., *J. Cell Biol.*, 132(3): 437-50, 1996). Hybridoma of B6H12 was purchased from the American Type Culture Collection (ATCC, Rockville, Md.) and has been previously described (Brown, et al., *J. Cell Biol.*, 111(6): 2785-94, 1990; Lindberg, et al., *J. Cell Biol.*, 123(2): 485-96, 1993; Blystone, et al., *J. Cell Biol.*, 130(3): 745-54, 1995). PF3.1 a new anti-CD47 mAb was developed in this laboratory using previously described procedures (Parkos, et al., *J. Cell Biol.*, 132(3): 437-50, 1996) by immunizing mice with CD47 immuno-purified from human splenocytes. Mouse IgG was purchased from Lampire Biological Laboratories (Pipersville, Pa.). Mouse IgG1 was purified by standard methods from mouse IgG fractions using Protein A sepharose. C5/D5 Fab was prepared by papain digestion of C5/D5 and undigested IgG and Fc were removed by protein A chromatography (Lampire Biological Labs). Purity of Fc fragments was confirmed by non-reduced SDS-PAGE.

Reagents and Buffers

Oligonucleotides for sequencing and for construct preparation were purchased from Gibco BRL, Life Technologies. Peptides were produced by solid phase synthesis at the Microchemical Facility, Winship Cancer Institute, Emory University School of Medicine. Peptides were analyzed by High Performance Liquid Chromatography (purity >90%) and Mass Spectrometry. Peptides were oxidized (>95%) by dissolving them in 0.1M $NH_4HCO_3$ pH 8.0 followed by stirring for 48 hours at room temperature. Cyclization was determined by MALDI and a negative Elman's test. Human CD47 was immuno-purified using C5/D5-sepharose as described previously (Parkos, et al., *J. Cell Biol.*, 132(3): 437-50, 1996) except that human splenocytes (50 gm) were used instead of epithelial cells. CD47 was eluted from the column using 50 mM triethylamine pH 10.5, 300 mM NaCl, 2 mM $MgCl_2$, 1% octylglucoside followed by immediate neutralization with Tris pH 7.4 (50 mM final).

MI3 Bacteriophage Libraries

Phage Libraries and bacterial strains-Four random phage-display libraries were used in this study. Two linear random nona-peptide phage library termed J404 and LL9 and two structurally constrained libraries displaying hexa- and decapeptide loops, called CL6 and CL 10 respectively were used. CL6, CL 10 and LL9 libraries were all produced in our laboratory (Mazzucchelli, et al., *Blood* 93(5): 1738-48, 1999). The 9-mer library, LL9 was constructed to replace our depleted stock of J404 using the original degenerate oligonucleotides used to construct J404 (Burritt, et al., *J. Biol. Chem.*, 270(28): 16974-80, 1995). J404 has been successfully used in the identification of several epitopes recognized by monoclonal antibodies and interactive regions on proteins (Burritt, et al., *J. Biol. Chem.*, 270(28): 16974-80, 1995; DeLeo, et al., *J. Biol. Chem.*, 270(44): 26246-51, 1995). All libraries were constructed using bacteriophage M13 with the random peptide sequences fused to the N-terminus of the minor coat protein pIII protein and have a kanamycin resistance cassette. *E. coli* strain K91 was used to propagate phage. The number of unique clones in the LL9 library was $3.66 \times 10^9$, similar to that reported for J404 ($5 \times 10^8$) and for CL6 and CL 10 libraries were $9 \times 10^8$ and $1.04 \times 10^9$ respectively.

Expression of Constructs CRE/DGWC in M13 Bacteriophage

Two complementary oligonucleotides coding for CRDGWC (SEQ ID NO:37) and CREGWC (SEQ ID NO:38), 5' ggaatgccgtggttggtgcggacctcctactgttg 3' (SEQ ID NO:39), 5'ctagcaacagtaggaggtccgcacca accatcccggcattccgc 3' (SEQ ID NO:40), and 5' ggaatgccgggagggttggtgcggac-ctcctactgttg 3' (SEQ ID NO:41), and 5' ggaatgcggttggcg-taatggtcagtcttgcggacctcctactgttg 3' (SEQ ID NO:42) respectively containing 5' Nhe 1 and 3' Sac II overhangs were annealed together as previously described (Burritt, et al., *J. Biol. Chem.*, 270(28): 16974-80, 1995) The annealed insert was ligated to Nhel- Sac II-digested M13 DNA and ligated DNA was transfected into electrocompetent *E.coli* K91 cells. Selected colonies were picked and their DNA prepared for sequencing. Phage having the correct sequence were propagated and analyzed for binding to mAb C5/D5 by ELISA as described below.

Antibody Phage Panning

Isolation of phage bearing epitopes bound by C5/D5 was performed as follows: Approximately $10^{10}$ Phage from J404, LL9, CL6 or CL 10 library were combined with 100 micro liter of a 1:1 slurry of Sepharose beads conjugated with C5/D5 (3 mg C5/D5/ml Sepharose) in phage buffer (50 mM Tris-Cl pH 7.4, 150 mM NaCl, 0.5% Tween 20 (v/v), 1 mg/ml BSA). Beads were mixed with phage at 4° C. overnight. Unbound phage were removed by washing the beads twice with 1 ml phage buffer, loading on a 5 ml plastic column (Fisher Scientific) and washed with 50 ml phage buffer. Bound phage were eluted from the beads with 1 ml 0.1 M glycine pH 2.2 and were immediately neutralized with saline/Hepes pH 10 (150 mM NaCl, 10 mM Hepes). An aliquot of the eluted phage was titered according to standard procedures. Three rounds of panning were performed with each library. As controls, three rounds of panning were also performed using Sepharose beads with no antibody coupled and Sepharose conjugated with normal mouse IgG (3 mg/ml). A sample of the bound phage eluted after three rounds of panning were sequenced for comparison.

Phage Amplification

Eluted phage were amplified in host K91 "starved" *E. coli* cells which were prepared, as described previously (Smith and Scott, 1990). Phage were amplified essentially as described on solid LB agar containing 75 μg/ml Kanamycin (Burritt, et al., *J. Biol. Chem.*, 270(28): 16974-80, 1995). After 24-36 hours incubation at 37° C., the colonies were suspended in 20 ml of saline/Hepes buffer pH 7.4 using a cell scraper (Costar, Cambridge, Mass. 02140). Phage were purified as described (Scott, et al., *Science* 249(4967): 386-90, 1990) and resuspended in 600 μl saline/Hepes buffer. Phage were titered and approximately $10^{10}$ phage were added to beads for a total of three rounds of affinity purification.

Plague Lift, Western Blot and DNA Sequencing

Eluted phage from third round panning were plated at a density of approximately 100 plaques per plate. Plaques were allowed to grow to approximately 1 mM in size and then lifted onto nitrocellulose paper. All subsequent incubations were at room temperature for one hour. Filters were placed in block buffer (5% low fat milk in TTBS) and then incubated with C5/D5 (24 μg/ml) in block buffer. Washed filters were then incubated with horsh radish peroxidase-conjugated rabbit anti-mouse IgG in block buffer (Jackson Immunoresearch Laboratories Inc.) followed by addition of substrate (ABTS-Hydrogen peroxide reagent, Amersham Pharmacia Biotech.) Positive staining plaques were picked, amplified, their DNA prepared and sequenced according to the directions of the Sequenase version 2.0 kit (US Biochemical Corp.) An oligonucleotide primer with the sequence 5'gcagaccttctgctgttttg 3' (SEQ ID NO:43) was used to determine the nucleotide sequence of the unique sequence of the phage. Sequencing gels were visualized using Biorad Multi-Analyst software.

Expression of CD47 Extracellular Domain in COS-7 Cells

The putative extracellular domain of human CD47 including the signal peptide was amplified by PCR using primers 5'-atgataagcttcctgcatgtggcccctggtagcgg-3 (SEQ ID NO:44) and 5'-ttgattagatctatttggagaaaaccatga-3' (SEQ ID NO:45) using reverse transcribed cDNA from T84 human intestinal epithelial cells. The DNA fragment was cloned into the mammalian expression vector AP-tag2 (Cheng, et al., *Cell*, 79: 157, 1994) that contains the catalytic domain of human placental alkaline phosphatase (AP) at the C-terminus through Bgl II and Hind III restriction sites. After transformation, at least three independent clones were isolated and the entire protein-coding region was confirmed by DNA sequencing. Transfection of COS-7 cells and subsequent CD47-AP fusion protein purification from cell culture medium were conducted as described previously.

ELISAs

Antibody phage binding assays were performed in microtiter plate wells (Limbro-Titertek, Flow Laboratories) which were coated with relevant antibodies (20 μg/ml) for two hours at room temperature. All subsequent incubations were performed at room temperature. After washing with saline/Hepes pH 7.4 (wash buffer), non-specific protein binding was blocked by incubation with block buffer (1% low fat milk in HBSS) for one hour. Amplified phage clones (109) were added in block buffer containing 0.1% Tween 20 (v/v) either in the absence or presence of increasing concentrations of peptide. After washing, wells were incubated with a 1:500 dilution of polyclonal rabbit anti-M13 phage antibody in block. Wells were washed again and incubated with a 1:1000 dilution of horse radish peroxidase conjugated goat anti-rabbit IgG (Organon Teknika Corp. West Chester, Pa.) and color developed using a solution of ABTS-Hydrogen peroxide. Microtiter wells were then analyzed in a microtiter plate reader at 405 nanometers (nm).

ELISA and In Vitro SIRPα1-CD47 Binding Assay 96 well microtiter plates were coated with SIRP-GST fusion protein for 2 h at room temperature (5 μg/ml). After blocking non-specific binding with 1% BSA (in HBSS (+)), monoclonal anti-SIRP antibodies were added at 10 μg/ml followed by incubation at room temperature for 30 min. After washing, the wells were incubated with peroxidase conjugated goat anti-mouse secondary and developed with the substrate ABTS. To assay CD47 binding to SIRP-GST, purified human CD47 (10-100 μg/ml in buffer containing 1% octylglucoside) was diluted 50-fold in HBSS in microtiter wells (50 μl) and allowed to bind for 2 h (room temperature). After blocking with BSA, the wells were incubated with SIRP-GST for 1 h. After washing, bound SIRP was assayed by incubation with goat anti-GST (Pharmacia) followed by peroxidase conjugated rabbit anti-goat secondary. CD47 extracellular domain binding to SIRP was assayed similarly except that SIRP-GST coated wells were incubated with CD47-AP fusion protein (2-10 μg/ml) for 30 min (room temperature) and binding detected by alkaline phosphatase activity.

PMN Transmigration Assay

PMN transepithelial migration experiments were performed using T84 intestinal epithelial cell monolayers as previously described (Liu, et al. *J. Biol. Chem.*, 276: 40156). Briefly, confluent T84 monolayers were washed twice with HBSS (20° C.). PMN ($1 \times 10^6$) in 150 μl HBSS with or without antibody was added to the upper chamber of the monolayer setup. Transmigration was initiated by transferring of PMN containing monolayers to 24-well tissue culture plates containing 1 ml of 1 μM fMLP in HBSS followed by incubation at 37° C. PMN migration across monolayers into the fMLP-containing lower chambers was quantified by myeloperoxidase (MPO) assay as previously described (Parkos, et al., *J. Cell Biol.*, 132(3): 437-50, 1996). Similar transmigration experiments were done with PMN migration across collagen-coated filters as previously described (Liu, et al. *J. Biol. Chem.*, 277(12): 10028-36, 2002).

Recombinant SIRPα1, SIRPβ1 and GST Fusion Proteins

The extracellular domain of SIRPα1, SIRPβ1 and GST fusion proteins were produced after transfected into 293E cells and purified as previously described (Seiffert, et al., *Blood*, 94: 3633, 1999; Seiffert, et al., *Blood*, 97: 2741, 2001).

CD47 Binding Assays

Microtiter plate wells were coated with 50,1 of purified Human CD47. Purified material (~100 μg/ml in 1% octylglucoside) was diluted 50-fold in HBSS followed by immediate addition of 501 to microtiter wells and incubated for 2 hours at room temperature. All subsequent incubations were for one hour at room temperature. After washing with saline/Hepes (wash buffer), wells were blocked with 0.5% BSA in HBSS. C5/D5 Fab was added (0.1 μg/ml) in the absence or presence of peptide in 0.5% BSA in HBSS. Wells were washed three times and incubated with horse radish peroxidase conjugated anti-mouse IgG (Fab)2 fragment specific (Jackson Immunoresearch, West Grove, Pa.): When using mAb C5/D5, peroxidase-conjugated goat anti-mouse IgG was used (Jackson Immunoresearch, West Grove, Pa.) After addition of a standard ABTS-Hydrogen peroxide reagent, wells were analyzed in a microtiter plate reader at 405 nm.

For CD47 and SIRPα1 binding assays, recombinant SIRPα1-GST fusion protein (containing the extracellular domain of SIRPα1) was generated as previously described. Microtiter plate wells were coated with SIRPα1-GST fusion protein (5 μg/ml) for two hours at room temperature. Wells were washed with HBSS and blocked with 1% BSA (in HBSS) for one hour. Peptide C5/D5.1 or control peptide was added for 30 min at RT. Fusion protein AP-CD47 (24 μg/ml) was added for 30 min. Plates were washed with HBSS and CD47 binding was analyzed by assaying AP activity with the substrate p-Nitrophenyl phosphate (Sigma) and analyzed in a microtiter plate reader at 405 nm.

In the case of C5/D5 Fab binding assays, after blocking, AP-CD47 fusion protein (2 µg/ml) with/without pre-incubated peptide/control peptide was added in the absence/presence of C5/D5 Fab fragment (0.1 µ/ml). After incubation for 30 min, the plates were washed with HBSS and CD47 binding was analyzed by assaying AP activity as described earlier.

General Cell Culture:

Epithelial cells: The T84 cell line is a transplantable human colonic carcinoma cell line established in nude mice that form polarized monolayers of columnar intestine-like epithelial cells, are functionally well differentiated and are a good model of epithelial cells of the intestinal crypt (Dharmsathaphom, et al., *Meth. Enzymol.* 192: 354; Madara, et al., *J. Clin. Invest.* 89: 1938; Madara, et al., *J. Clin. Invest.* 91: 2320; Parkos, et al., *J. Cell. Biol.* 117: 757). T84 cells are grown as monolayers in a 1:1 mixture of Dulbecco-Vogt modified Eagles medium and Hanks F-12 medium supplemented with 15 mM HEPES buffer (pH 7.5), 14 mM NaHCl$_3$, 40 mg/ml penicillin, 8 mg/ml ampicillin, 90 mg/ml streptomycin and 5% newborn calf serum. Monolayers are subcultured (or harvested) every 7-14 days by trypsin treatment with 0.1% trypsin and 0.9 mM EDTA in Cams and Mgr' free phosphate buffered saline. Other epithelial cell lines (Caco2, A549, HT29, CF 15 etc.), including non transformed renal cell lines such as MDCK are in routine use within the Epithelial Cell Biology Unit at Emory and readily available Hybridomas: Hybridomas are maintained in suspension in RPMI supplemented with 10% FBS, 2 mM L-glutamine, 40 mg/ml penicillin, 90 mg/ml streptomycin, 10 mM HEPES, and non-essential amino acids (Gibco BRL). Cells are subcultured in 165 cm$^2$ flasks every 2-3 days after reaching densities of ~2-6×10$^5$/ml. As needed, new SIRP mAbs can be produced by immunizing Balb c with SIRP fusion proteins produced as detailed in AIM 1. Splenocytes from immunized mice are fused with P3U1 myeloma cells and cultured in selection media containing DBA-2 feeder thymocytes. Hybridomas will be screened for reaction with SIRP fusion proteins by EISA in concert with cell surface staining. Hybridomas will then be subcloned by limiting dilution, weaned from selection media and either grown in roller bottles for bulk antibody production or, if mAb yields are low, injected into the peritoneal cavities of balb C mice for ascites fluid production.

Neutrophil Isolation

Briefly, human PMN are obtained from whole blood from normal human volunteers after anticoagulation with citrate. Neutrophils are isolated by dextran sedimentation followed by Ficoll-Hypaque separation using standard techniques. Residual RBC were lysed with isotonic NH4Cl. Isolated PMN are then resuspended in Hanks balanced salt solution devoid of calcium or magnesium (4° C.) and are used within 4 hours.

Antibody Purification/Immunoprecipitations/Immunoblotting

IgG will be purified from ammonium sulfate cuts of cell culture supernatants or ascites fluids using protein A-Sepharose by standard methods. Antibody fragmentation will be performed by standard papain/pepsin digestion techniques. Alternatively, antibody fragmentation services are available through Lampire Biological Corp. For immunoprecipitation and immunopurifications, purified IgG will be covalently coupled to CNBr-activated Sepharose at a density of 2-3 mg/ml of beads as described by the manufacturer (Pharmacia). Standard immunoprecipitations will be performed using immobilized antibodies and detergent extracts of cells, which have been pre-cleared with irrelevant mouse IgG-Sepharose. Samples are subjected to SDS polyacrylamide gel electrophoresis and transferred to nitrocellulose using a standard Western blotting protocol. Transblotted proteins are visualized by enhanced chemiluminescence after incubation with primary antibodies and peroxidase conjugated secondary antibodies.

Purification of CD47

Human CD47 is purified from human red blood cells (RBC), PMN, spleen and HT-29 intestinal epithelial cells as previously described (Parkos, et al., *J. Cell Biol.*, 132: 437). Briefly, suspensions of RBC (from 120 ml blood), PMN (~10$^{10}$), and HT-29 (5×10$^9$) cells are directly lysed in buffer (1% octylglucoside, 100 mM NaCl, 2 mM of each CaCl$_2$ and MgCl$_2$ in 100 mM Tris/HCl, pH 7.5) containing a cocktail of protease inhibitors. Human spleen (30 g) obtained from autopsy material is homogenized by douncing (20 strokes) in the same lysis buffer. After low speed (1000×g) and high speed (100,000×g) centrifugation, supernatants are subjected to immunoaffinity chromatography using anti-CD47 mAb C5/D5 or PF3.1 conjugated to Sepharose (2 mg of IgG/ml as described by the manufacturer (Pharmacia)). After washing with lysis buffer, CD47 is eluted with 50 mM TEA, 1% octylglucoside, 100 mM NaCl, pH 10.5 followed by neutralization, dialysis and concentration.

Production of Recombinant CD47-Alkaline Hosphatase (CD47-AP) Fusion Protein

A construct consisting of the extracellular domain of human CD47 fused to the catalytic domain of human placental AP was prepared using the AP-tag2 (Jiang, et al., *J. Biol. Chem.*, 274: 559; Cheng, et al., *Cell* 79:157) expression vector. The CD47-AP construct was subcloned from AP-tag2 into the tetracycline-response element containing pTRE2 vector (Clontech) and co-transfected into CHO-K1 cells with a plasmid (Kn1StTA) consisting of a Tet-Off transactivator containing a nuclear localization signal cloned into the pIRES 1neo vector (Clontech). Clones were picked after 6418 selection and assayed for AP activity. Expressed CD47-AP fusion protein in medium is affinity purified using PF3.1-Sepharose and eluted with 50 mM TEA, pH 10.5, 150 mM NaCl followed by neutralization, concentration and dialysis. A second control AP fusion protein containing the extracellular domain of junctional adhesion molecule (JAM) was produced and is purified by similar methods.

Morphologic Studies/Immunofluorescence

Surface CD47 and SIRP labeling are performed by incubation of 100 µl of non-permeabilized PMN or other cells (5×10$^6$ cells) with mAb (20 µg/ml) for 1 h at 4° C. in HBSS after blocking non-specific binding with 0.5% BSA. After washing, cells are incubated with FITC conjugated goat anti-mouse secondary antibody (1:200 dilution in HBSS) (Pharmingen) for 30 min at 4° C. followed by wash before flow cytometric analysis. CD47 and SIRP labeling in this condition are compared to that observed with isotype-matched IgG.

For immunfluorescence of transfected cells or epithelial monolayers, cells will be fixed in 3.7% paraformaldehyde in phosphate buffered saline (PBS), washed, and most preparations will be permeabilized in ethanol at −20° C. or in 0.1% triton X-100 for 1-5 minutes. Subsequently, samples will be washed with gelatin-PBS, incubated with primary antibody for 1-3 hr (20° C.), washed with gelatin-PBS and followed by incubation with rhodamine or fluorescein labeled secondary antibody for 1 hour. After washing, the monolayers or sections will be mounted for fluorescence microscopy.

It should be emphasized that the above-described embodiments of the present invention are merely possible examples of implementations, and are set forth only for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

Therefore, having thus described the invention, at least the following is claimed:

1. An isolated polypeptide, consisting of an amino acid sequence selected from: the amino acid sequence set forth in SEQ ID NO:2; the amino acid sequence set forth in SEQ ID NO:4; and the amino acid sequence set forth in SEQ ID NO:6.

2. A fusion polypeptide consisting of a heterologous polypeptide and the polypeptide of claim 1.

3. The isolated polypeptide of claim 1, wherein the polypeptide inhibits the interaction of SIRPα with CD47.

* * * * *

UNITED STATES PATENT AND TRADEMARK OFFICE
CERTIFICATE OF CORRECTION

| | | |
|---|---|---|
| PATENT NO. | : 7,282,556 B2 | Page 1 of 2 |
| APPLICATION NO. | : 10/473495 | |
| DATED | : October 16, 2007 | |
| INVENTOR(S) | : Parkos | |

It is certified that error appears in the above-identified patent and that said Letters Patent is hereby corrected as shown below:

Column 9, line 16, delete "that is mixture" and replace with --that is a mixture--

Column 13, line 43, delete "by" and replace with --be--

Column 13, line 50, delete "cytotxic" and replace with --cytotoxic--

Column 14, line 33, delete "polypeptide" and replace with --polypeptides--

Column 16, line 28, delete "polynucleotides" and replace with --polynucleotide--

Column 18, line 30, delete "methods" and replace with --method--

Column 20, line 25, delete "57, about" and replace with --57%, about--

Column 21, line 15, delete "preferably about" and replace with --preferably to about--

Column 23, line 48, delete "which." and replace with --which--

Column 25, line 24, delete "can delivered" and replace with --can be delivered--

Column 25, line 64, delete "pharmaceutical" and replace with --pharmaceutically--

Column 30, line 11, delete "and other" and replace with --and the other--

Column 32, line 11, delete "may required" and replace with --may be required--

Column 33, line 37, delete "contrary, same" and replace with --contrary, the same--

Column 34, line 45, delete "that involved" and replace with --that are involved--

Column 34, lines 61-62, delete "on surface" and replace with --on the surface--

Column 35, line 54, delete "phages are bind" and replace with --phages bind--

UNITED STATES PATENT AND TRADEMARK OFFICE
CERTIFICATE OF CORRECTION

PATENT NO. : 7,282,556 B2
APPLICATION NO. : 10/473495
DATED : October 16, 2007
INVENTOR(S) : Parkos It is certified that error appears in the above-identified patent and that said Letters Patent is hereby corrected as shown below:

Column 36, line 21, delete "trptophan" and replace with --tryptophan--

Column 37, line 15, delete "is" and replace with --does--

Column 38, line 32, delete "1995) The" and replace with --1995). The--

Column 41, line 30, delete "available" and replace with --available.--

Signed and Sealed this

Thirteenth Day of May, 2008

JON W. DUDAS
*Director of the United States Patent and Trademark Office*